United States Patent [19]

Woyciesjes et al.

[11] Patent Number: 5,422,008
[45] Date of Patent: * Jun. 6, 1995

[54] REINHIBITION OF RECYCLED ANTIFREEZE/COOLANT

[75] Inventors: Peter M. Woyciesjes, Woodbury; Aleksei V. Gershun, Danbury; Stephen M. Woodward, Lakeside, all of Conn.

[73] Assignee: First Brands Corporation, Danbury, Conn.

[ * ] Notice: The portion of the term of this patent subsequent to Jun. 29, 2010 has been disclaimed.

[21] Appl. No.: 160,374

[22] Filed: Nov. 23, 1993

Related U.S. Application Data

[63] Continuation of Ser. No. 702,649, May 17, 1991, abandoned.

[51] Int. Cl.$^6$ .............................................. C02F 1/52
[52] U.S. Cl. ............................ 210/662; 210/665; 210/667; 210/669; 210/688; 210/724; 210/739; 210/743; 210/805; 210/806
[58] Field of Search ................ 210/665, 664, 96.1, 210/662, 666–669, 739, 724, 167, 688, 726–728, 743, 806, 805; 73/61.1 R; 422/7

[56] References Cited

U.S. PATENT DOCUMENTS

| | | | |
|---|---|---|---|
| 3,805,880 | 4/1974 | Lawlar | 210/696 |
| 4,160,740 | 7/1979 | Sweet | 252/75 |
| 4,210,547 | 7/1980 | Hirozawa et al. | 252/75 |
| 4,234,440 | 11/1980 | Hirozawa et al. | 252/75 |
| 4,260,827 | 4/1981 | Klinkmann el al. | 210/664 |
| 4,357,243 | 11/1982 | Dobrez et al. | 210/764 |
| 4,532,045 | 7/1985 | Littmann | 210/167 |
| 4,793,403 | 12/1988 | Vataru et al. | 210/167 |
| 4,931,187 | 6/1990 | Deeham et al. | 210/96.1 |
| 4,946,595 | 8/1990 | Miller, Jr. | 210/651 |
| 5,021,152 | 6/1991 | Filowitz et al. | 210/167 |
| 5,078,866 | 1/1992 | Filowitz et al. | 210/167 |
| 5,094,757 | 3/1992 | Light | 210/765 |
| 5,174,902 | 12/1992 | Shubert et al. | 210/662 |

Primary Examiner—Cynthia L. Nessler
Attorney, Agent, or Firm—Gary L. Wamer

[57] ABSTRACT

The process relates to the reinhibition of recycled antifreeze/coolant. The process is particularly well suited for use with recycled, used antifreeze/coolant from the cooling systems of internal combustion engines.

48 Claims, No Drawings

REINHIBITION OF RECYCLED ANTIFREEZE/COOLANT

This application is a continuation of prior U.S. application Ser. No. 07/702,649, filed May 17, 1991, now abandoned.

FIELD OF THE INVENTION

The instant invention relates to the reinhibition of recycled, used antifreeze/coolant from the cooling systems of internal combustion engines whereby corrosion protection is provided in an effective corrosion inhibiting amount. The reinhibited, recycled antifreeze/coolant may then be reintroduced into a cooling system as an "original" antifreeze/coolant. The instant invention is particularly useful in treatment of recycled antifreeze/coolant removed from cooling systems of internal combustion systems.

INFORMATION DISCLOSURE STATEMENT AND BACKGROUND

The prior art relating to the purification of aqueous solutions of ethylene glycol and to corrosion inhibitors for used antifreeze/coolant compositions will be discussed hereinafter.

PURIFICATION OF ANTIFREEZE/COOLANT

U.S. Pat. No. 3,732,320 discloses a purification process for reducing the iron content of ethylene glycol from an ethylene glycol manufacturing process. The process involves contacting ethylene glycol with a cation exchange resin in the acid cycle. Although the removal of iron was of primary concern to the patentee, the patentee generally states that "iron and other metallic contaminants present in trace amounts" may be removed by the cation exchange treatment.

U.S. Pat. No. 4,118,582 discloses a recovery process for removing dissolved antimony catalyst from unreacted ethylene glycol recovered from the manufacture of polyester. The recovery process involves a pH adjustment of the spent glycol to about 2 to 7, reaction with an alkali metal borohydride to form a metallic antimony precipitate, separation of the metallic antimony precipitate from the spent glycol (unreacted ethylene glycol from the manufacture of polyester) in the absence of oxygen, followed by distillation of ethylene glycol from the spent glycol.

U.S. Pat. No. 4,260,827 discloses a process for the purification of aqueous solutions of low molecular weight polyhydroxyl compounds. The patentee's process is directed to the purification of low molecular weight polyhydroxyl compounds after their manufacture in the presence of catalysts containing calcium and/or lead. The patentee's process involves numerous treatment and distillation steps. The aqueous solution of the low molecular weight polyhydroxyl compound is first treated with methanol and a precipitant to form a precipitate to be separated from a residual solution. The pH of the methanol/precipitant solution of low molecular weight polyhydroxyl compounds may be adjusted to a pH from 1 to 4 to maximize precipitation of the calcium and/or lead compounds from the methanol treated solution. The deposits (precipitates) are removed by filtration and the residual solution treated with a cation exchanger. The residual solution is then distilled to remove low-boiling fractions. The distillation sump essentially containing the low molecular weight polyhydroxyl compounds is then treated with an anion exchanger.

The above processes have been directed to manufacturing processes where a manufactured product is being purified or where there is a need to purify and recover unreacted raw materials from specific reagents present as a result of commercial processes. Such processes deal with purification of compositions with limited and well understood contaminants.

The purification of more ethylene glycol-containing streams from automotive cooling systems raises significantly more complex questions as to the contaminants to be removed by treatment. For example, the purification of a spent antifreeze/coolant is a dramatically different treatment process owing to the novel and harsh environment to which the antifreeze/coolant has been subjected and, further, owing to the specific and unique chemical components commonly present in the spent antifreeze/coolant to be treated. Owing to the complexities associated with treating a spent antifreeze/coolant it is not surprising that few attempts have been made to treat spent antifreeze/coolant solutions.

U.S. Pat. No. 4,791,890 discloses a flushing process (employing a flushing liquid having entrained gas bubbles) for an automotive cooling system wherein the patentee includes a filtering step (at 302). The patentee provides no other treatment of the spent antifreeze coolant. U.S. Pat. No. 4,793,403 discloses a coolant system for use in treatment of coolant liquid. The liquid coolant is treated by filtering to remove contaminant from the coolant liquid. The patentee discusses a chemical treatment at column 3, lines 11 to 28, but only in vague terms and only by addition of chemical components previously present in the original antifreeze/coolant, i.e., addition of new additives. The patentee discloses removal of particulate and congealed substances through a filter (28) followed by treatment of aqueous liquid by addition of chemical agent or agents. The patentee does not disclose any particular treatment, merely alluding to the fact that such chemicals can include corrosion inhibitor, i.e., anti-rust compound, pH adjustment chemicals, and fresh antifreeze compound (glycol, for example). In addition, at column 3, lines 38 to 48, filter 41 may contain "metal powder" to provide metallic ions for neutralizing electrical charge. Similarly, Kleer-Flo Company has published the details of a antifreeze recycle machine (Kleer-Flo AF 250 Anti-Freeze Recycler) which employs a three step filtration system which employs a stainless steel screen filter, a pre-filter for removing materials down to a size of 5 microns and a third filter alleged to remove impurities at the molecular level (approximately 50 Angstoms). After filtration the filtered antifreeze is mixed with an additive package to provide a working antifreeze for reintroduction into an automotive cooling system. No chemical removal process is disclosed whereby the purification of the spent antifreeze/coolant is achieved.

U.S. Pat. No. 4,946,595 discloses a process for physically and chemically treating a used coolant to remove unwanted impurities, degradation by-products, dissolved metals dirt, silt and other unwanted suspended particulate matter. The process involves: the oxidation of metal components to form particulate metallic oxide precipitates, contacting the coolant with salt forming agents for reaction with organic acids; filtering the coolant to remove particulate precipitates; adding corrosion inhibiting agents selected from the group consisting of phosphates, phosphonates, silicates, borates, nitrites, nitrates, azols, modified 'acrylates' and molybdates and adjusting the pH to between 9.5 and 10.5, . . . "Thereby providing a recycled coolant composition having corrosion capabilities equal or superior to that of the original coolant composition prior to removal." This process fails to appreciate the characteristics of the recycled antifreeze/coolant (or any other factor) in providing a reinhibited, recycled spent antifreeze.

The above discussion of the prior art demonstrates the failure of the prior art to disclose an effective process for the purification of used ethylene glycol-based heat exchange fluids, particularly used spent antifreeze/coolant from automotive cooling systems. It is particularly useful to note the lack of effective treatment steps of the spent antifreeze/coolant in U.S. Pat. No. 4,793,403 and by the Kleer-Flo AF 250 Anti-Freeze Recycler for contaminants such as heavy metals and organic compounds other than ethylene glycol. Further, such processes specifically warn against their use when the spent antifreeze/coolant to be treated contains an oil component. Such a limitation of use significantly detracts from the commercial use of such processes.

REINHIBITION OF RECYCLED ANTIFREEZE/COOLANT

Although considerable prior art exists as to the use of effective amounts of corrosion inhibitors for addition to virgin-ethylene glycol, very little prior art exists as to the reinhibition of a treated used antifreeze/coolant. One recent patent dealing with a process for treatment of used antifreeze/coolant is U.S. Pat. No. 4,946,595. In addition to a treatment process, the patentee discloses the addition of: any suitable corrosion inhibitor selected from the group consisting of phosphates, phosphonates, silicates, borates, nitrites, nitrates, azols, modified acrylates and molybdates; and known buffering agents to adjust the pH of the final solution to between about 9.5 and 10.5. The patentee's goal is to provide a recycled coolant composition having corrosion capabilities equal or superior to that of the coolant in the engine cooling system prior to the physical and chemical treatment and the addition of corrosion inhibiting agents with final pH adjustment to between about 9.5 and 10.5. The patentee discloses (column 5, lines 51–63) a general characterization of known corrosion inhibitors with no appreciation of the interrelationship of such and without any appreciation of the relationship of the use of corrosion inhibitors and the chemical composition of the recycled, used antifreeze/coolant. The patentee discloses that all the process components (oxidizing agents, salt forming agents, corrosion inhibitor(s) and buffering agent(s)) may be added to the used antifreeze/coolant as one chemical composition (column 5, lines 51 to 54). This disclosure demonstrates that the patentee does not appreciate the intricate complexities of corrosion reinhibition of a recycled, used antifreeze/coolant. Further use of a single chemical additive composition for addition to an untreated, used antifreeze/coolant demonstrates that the patentee is failing to recognize any interaction as to the components of the single chemical additive and has clearly considered the used antifreeze/coolant to be equivalent to virgin grade antifreeze/coolant for the purpose of determining how to add corrosion inhibitors. Since the patentee is only seeking to have corrosion protection equivalent to the used antifreeze/coolant (which is being replaced owing to it not being as good as the original antifreeze/coolant as a result of use) it is assumed by the patentee that reinhibition with corrosion inhibitors at concentrations employed to inhibit virgin ethylene glycol will be acceptable. Further, the patentee in the example demonstrates the use of a fixed concentration chemical additive composition where the amount which is added is based only upon the pH of the final antifreeze/coolant without any adjustment in the concentrations of the corrosion inhibitors. This lack of appreciation of the history of a recycled, used antifreeze/coolant results in a reinhibited coolant having corrosion inhibiting characteristics which are a result of mere happenstance. This is quite apparent when one recalls that the patentee requires only that the final reinhibited, treated coolant be as good as the used antifreeze/coolant removed from the engine cooling system and that the used antifreeze/coolant is being removed from the cooling system because it is no longer effective in protecting the cooling system from corrosion.

SUMMARY OF THE INVENTION

The instant invention relates to a process for the reinhibition of a recycled used antifreeze/coolant which has been recycled after use in the cooling system of an internal combustion engine. The chemical and physical characteristics of recycled, used antifreeze/coolant have been found to create a unique problem when employed to provide a reinhibited, recycled antifreeze/coolant for reuse in a cooling system of an internal combustion engine. It has been found that heretofore employed chemical compositions and manufacturing processes for the manufacture of antifreeze/coolant from virgin ethylene glycol do not provide antifreeze/coolant compositions with effective corrosion inhibiting properties when recycled antifreeze/coolant is employed in the place of virgin ethylene glycol.

The instant invention solves the aforementioned problem by providing a "reinhibition package" that is correlated to the use history of the antifreeze/coolant. By correlating the desired effective corrosion inhibiting characteristics of the reinhibited, recycled antifreeze/coolant to the residual chemical components of the particular recycled antifreeze/coolant, the effective corrosion inhibiting characteristics of the final reinhibited, recycled antifreeze/coolant may be improved as compared to that obtained by indiscriminatingly adding corrosion inhibitors to a recycled antifreeze/coolant without taking into account the characteristics of the recycled, used antifreeze/coolant. The concentration of silicate, reserve alkalinity and corrosion inhibitors in the recycled, used antifreeze/coolant as a result of the particular recycle process are correlated to the concentration of the chemical components in the reinhibitor package to form a reinhibited, recycled, used antifreeze/coolant and, further, is obtained at a lower effective cost. The details of this correlation and the properties of the reinhibitor package and reinhibited, recycled, used antifreeze/coolant will be discussed hereinafter.

The instant invention appreciates for the first time that the "chemical fingerprint" of the recycled antifreeze/coolant (based upon the particular recycle process from which it was derived) must be correlated to the desired effective corrosion inhibiting properties of the final reinhibited, recycled antifreeze/coolant and that the concentrations of the components in the reinhibitor package will reflect this correlation.

The instant reinhibition process is employed using recycled, polyhydric alcohol-containing antifreeze/coolants. In one embodiment the used antifreeze/coolants is from a heat exchange system of an automotive internal combustion engine having between about 5 weight percent and about 95 weight percent ethylene glycol, and contains at least one metal, typically a heavy metal, and/or an oil component to be removed. A recycle process useful in this embodiment and generally comprising the following steps is disclosed in U.S. Ser. No. 07/564,262:

(i) adjusting the pH of said polyhydric alcohol-containing composition to between about 4.0 and about 7.5 by addition of an effective amount of an pH adjusting agent to form a pH-adjusted composition; and (ii) adding an effective amount of a precipitating agent for at least one metal, preferably at least one heavy metal, and/or oil component present in the pH-adjusted composition; and (iii) preferably also includes adding to the pH-adjusted composition of step (ii) an effective amount of a coagulating agent and an effective amount of a flocculating agent effective in forming a precipitate containing at least one metal; and (iv) passing the pH-adjusted composition through a first filtration means to remove a major amount of said metal-containing precipitate and, optionally, physical skimming of the surface of said pH-adjusted composition to remove precipitate at said surface.

In addition to the above steps the recycle process of U.S. Ser. No. 07/564,262 (filed Aug. 8, 1990) may also include one or more of the following steps:

(v) passing the pH-adjusted composition from the first filtration means through a second filtration means effective in the physical separation of particles of a smaller size that said first filtration means;

(vi) passing the pH-adjusted composition after the second filtration means through an organic separation means effective in removing organic compounds (other than the polyhydric alcohol(s)) from the pH-adjusted composition;

(vii) passing said pH-adjusted composition through a third filtration means having an effective physical separation of particles by size smaller than said second filtration means; and (viii) passing said pH-adjusted composition after filtration through an ion exchanger anion and/or cation effective in the removal of at least one solubilized metal, preferably heavy metal, from said pH-adjusted composition.

As discussed hereinafter, other recycle processes for used antifreeze/coolant may be employed to provide the recycled antifreeze/coolant which may be reinhibited according to the instant invention.

DETAILED DESCRIPTION OF THE INVENTION

Considerable interest has been associated with the recycle of antifreeze/coolant from cooling systems of internal combustion engines. In particular, the recycle of such aqueous ethylene glycol mixture has received considerable attention owing to the disposal of used (often referred to as "spent") antifreeze/coolant. Ideally, a used antifreeze/coolant would be recycled by both physically and chemically treating the used antifreeze/coolant to remove degradation products and other chemical components present in the antifreeze/coolant, e.g., corrosion inhibiting components in the original antifreeze/coolant, and then providing a "reinhibitor package" for the recycled antifreeze/coolant whereby an antifreeze/coolant is formed for use in the same capacity as an antifreeze/coolant manufactured from virgin ethylene glycol. The "reinhibitor package" must provide chemical components effective in inhibiting corrosion of metals present as an integral part of cooling systems so as to provide a reinhibited, recycled antifreeze/coolant effective in inhibiting the corrosion of metals in the cooling systems. Several recycle processes for used antifreeze/coolant have been considered. Representative recycle processes for used antifreeze/coolant are exemplified in copending U.S. Ser. No. 07/564,262, filed Aug. 8, 1990, entitled, "PROCESS FOR TREATMENT OF AQUEOUS SOLUTIONS OF POLYHYDRIC ALCOHOLS" and in U.S. Pat. No. 4,946,595. Recycled antifreeze/coolants from such recycle processes provide water/ethylene glycol mixtures having unique chemical characteristics which are directly related to previous use as an antifreeze/coolant for an internal combustion engine and the recycle process from which it was obtained. This unique use history and the resulting characteristics of the recycled antifreeze/coolant have not heretofore been taken into account in determining the "reinhibitor package" to be employed in providing an effective corrosion inhibiting amount of corrosion inhibitors for a recycled spent antifreeze/coolant. For example, U.S. Pat. No. 4,946,595 describes (beginning at column 5, line 64 et seq) that the corrosion inhibitors may be any known corrosion inhibitor. Further, as noted in Example 1 and the claims, the patent preferably adds the corrosion inhibitors with total disregard to any consideration of the interrelation of the components of the "reinhibitor package" and, further, does not consider the selection of the relative concentrations of the chemical components in relationship to the use history of the recycled spent antifreeze/coolant and residual chemical components present in the recycled, used antifreeze/coolant.

The instant invention overcomes the deficiencies of the prior art and relates to a process for the reinhibition of a recycled used antifreeze/coolant which has been recycled after use in the cooling system of an internal combustion engine. The chemical characteristics of recycled used antifreeze/coolant have been found to provide unique problems when employed to provide a reinhibited, recycled, used antifreeze/coolant for reuse in a cooling system of an internal combustion engine. It has been found that heretofore employed concentrations of corrosion inhibitors for the manufacture of antifreeze/coolant from virgin ethylene glycol do not provide antifreeze/coolant compositions with the desired effective corrosion inhibiting properties when recycled antifreeze/coolant is employed in the place of virgin ethylene glycol. Further, the cost of manufacturing an antifreeze/coolant from a recycled antifreeze/coolant can be substantially decreased according to the instant invention by correlating the reinhibitor package to the chemical fingerprint of the recycled antifreeze/coolant.

The instant invention solves the aforementioned problem by providing a "reinhibition package" that is correlated to the use history of the antifreeze/coolant. By correlating the desired effective corrosion inhibiting characteristics of the reinhibited, recycled antifreeze/coolant to the residual chemical components of the particular recycled antifreeze/coolant the effective corrosion inhibiting characteristics of the reinhibited, recycled antifreeze/coolant may be improved as compared to that obtained by indiscriminatingly adding corrosion inhibitors to a recycled antifreeze/coolant without taking into account the chemical characteristics of the antifreeze/coolant. Concentration parameters such as the concentration of silicate, reserve alkalinity and corrosion inhibitors of the recycled, used antifreeze/coolant and the concentration of chemical components in the reinhibitor package are correlated by the process of the instant invention to provide a reinhibited antifreeze/coolant having effective corrosion inhibiting properties for reuse in a cooling system. The details of this correlation and the resulting chemical and physical properties of the reinhibitor package and reinhibited, recycled antifreeze/coolant will be discussed hereinafter and demonstrated in the examples.

At the outset it is important to appreciate the unique characteristics of used antifreeze/coolants when such are removed from cooling systems of internal combustion engines for recycle. Further, it is important to appreciate that the term "recycled" as employed herein is in part defined by economic ease of use, since certain purification and treatment processes are excluded from those employed to provide a "recycled" antifreeze/coolant owing to their nature. The term "recycled" as employed herein in relation to treatment of used antifreeze/coolant includes: chemical treatment processes wherein one or more chemical additives is added to the used antifreeze/coolant to remove or stabilize chemical components in the used antifreeze/coolant; physical separation (e.g., filtration or separation by centrifreeze) to remove particular material; adsorption and absorption processes to remove one or more chemical components from the aqueous polyhydric alcohol; cation and/or anion exchange processes; and other processing steps which result in a change in the compositional profile ("chemical fingerprint") of the used antifreeze/coolant. The term "recycled" does not include a process which begins with a used antifreeze/coolant and by means of chemical treatment, dehydration or distillation results in a final product substantially the same as nonaqueous polyhydric alcohol, e.g., substantially pure, virgin ethylene glycol sans chemical components found in used antifreeze/coolant. Since the previous use environment of the spent antifreeze/coolant is of importance in understanding the correlation of the recycled antifreeze/coolant to the reinhibitor package, a discussion of this use environment is discussed hereinafter.

ANTIFREEZE/COOLANTS AND COOLING SYSTEMS

The term "heat exchange system" is employed herein to include any heat exchange system and includes "cooling systems" for internal combustion engines, as commonly employed in automobiles, trucks, motorcycles, airplanes, trains, tractors, generators, compressors and the like. The cooling system in automobiles and trucks are representative of such heat exchange systems for internal combustion engines. Automotive heat exchange systems and their construction are well known in the art and are known to contain several metals, including aluminum and lead solder which with time may be dissolved into the working antifreeze/coolant composition within the cooling system by physical abrasion and/or chemical action. The term "used antifreeze/coolant" herein refers to an antifreeze/coolant which has operated as the antifreeze and/or coolant for a time in a heat exchange system, including an automotive cooling system.

The term "metals" as used herein in reference to the metal components present in the spent antifreeze/coolant includes metals such as aluminum and magnesium and "heavy metals" such as lead, iron, zinc, manganese, copper and molybdenum. Although aluminum is not a "heavy" metal as that term is understood in the prior art, the term "heavy metal" as used herein is intended to include aluminum as to the metal components present in a spent antifreeze/coolant which are subject to removal by the instant process. Owing to the construction of a cooling system, as a result of aluminum surfaces being in contact with a working antifreeze/coolant, it is common for the spent antifreeze/coolant to contain aluminum.

The antifreeze/coolant employed in heat exchange systems is generally a mixture of various chemical components and an alcohol (including methanol, ethanol, propanol, butanol, ethylene glycol, diethylene glycol, propylene glycol, dipropylene glycol, glycerol, butene glycol, the monoacetate of propylene glycol, the monoethylether of glycol, the dimethyl ether of glycerol, alkoxy alkanols and mixture thereof); with the preferred alcohols being selected from the group consisting of ethylene glycol, diethylene glycol, propylene glycol, dipropylene glycol and mixtures thereof. Commercially available antifreeze/coolants generally consist of ethylene glycol, water and additional chemical components which provide corrosion protection or other beneficial benefits for the particular heat exchange system(s) wherein it is employed. Further, it is well known that up to about 10% diethylene glycol or higher may be present in the grade of ethylene glycol employed to manufacture commercial antifreeze/coolants.

Owing to the wide spread use antifreeze/coolants in internal combustion engine cooling systems based upon ethylene glycol/water mixtures, the instant invention takes into account the wide range of compositions used heretofore in conjunction with ethylene glycol-based antifreeze/coolants heretofore employed as heat exchange fluids for the cooling systems of internal combustion engines. Representative ethylene glycol-based antifreeze/coolants are those containing silicone/silicate additives and/or various carboxylic acids as corrosion inhibitors for the automotive cooling systems. Other optional additives are typically employed in commercial antifreeze/coolants in minor amounts of less than 50 wt. percent based on the weight of the antifreeze/coolant. Typical optional additives included in antifreeze/coolants include, for example, are known corrosion inhibitors for aluminum or other metals in admixture with the oils and the hydrophobizing agents of the present invention such as, for example, molybdates, mono and/or di-aliphatic acids, e.g., sebacates, carbonates, silicates, alkali metal nitrates, alkali metal nitrites, diisopropylamine nitrite, dicyclohexylamine nitrate, tolyltriazole, mercaptobenzothiazole, benzotriazole, zinc compounds, calcium compounds, phosphates, benzoates, and the like, or mixtures thereof. Further, one or more of these known inhibitors for various metals are in an "inhibitory effective amount", i.e., an amount sufficient to provide a measurable amount of corrosion inhibition with respect to the metal (e.g., copper, steel, brass, aluminum, cast iron, solder, etc.) surfaces to be protected as compared to the corrosion protection provided by the antifreeze/coolant without these inhibitors. Other optional additives that may be present in commercial antifreeze/coolants include: wetting agents and surfactants such as, for example, known ionic and non-ionic surfactants such as the poly(oxyalkylene) adducts of fatty alcohols; defoamers and/or lubricants such as the well-known polysiloxanes and the polyoxyalkylene glycols; wear inhibitors, such as the zinc dithiophosphates and the zinc thiocarbamates; lubricants, such as silicone pump lubricants; and other ingredients known in the art of antifreeze/coolants that do not adversely affect the antifreeze/coolant characteristics sought to be achieved by the end use of the antifreeze/coolant.

Representative antifreeze/coolant compositions based upon polyhydric alcohols which may be treated according to the instant invention after use in a heat exchange system, i.e., when collected after use (e.g., a "spent" or "used" antifreeze/coolant from an automotive cooling system) include, but are not limited to, those described in U.S. Pat. Nos. 4,664,833, 4,287,077, 4,725,405, 4,704,220, 4,684,474, 4,685,475, 4,687,590, 4,701,277, 4,561,990, 4,578,205, 4,584,119, 4,587,028, 4,588,513, 4,592,853, 4,629,807, 4,647,392, 4,657,689, 4,759,864, 4,851,145, 4,810,406 and 4,345,712; the aforementioned patents incorporated herein by reference. In the aforesaid patents are disclosed combinations of chemical components effective in protecting the metal surfaces of such cooling systems, such being generally referred to as an "inhibitor package."

The spent antifreeze/coolant mixtures obtained by removal from heat exchange systems of internal combustion engines are generally characterized as containing ethylene glycol or other polyhydric alcohol(s) and are typically a mixture containing between about 5 volume percent and about 95 volume percent ethylene glycol and/or other polyhydric alcohol, preferably between about 30 volume percent and about 70 volume percent. The actual amount of ethylene glycol and/or other polyhydric alcohol present in the antifreeze/coolant will depend on several factors. For example, during the "change-over" of an antifreeze/coolant in the cooling system of an internal combustion engine the cooling system will be emptied and the removed antifreeze/coolant placed in a collection container. The cooling system will typically then be flushed with water and/or water with a minor amount of a cleaning agent. This substantially water solution will typically be emptied into the same holding container as the original spent antifreeze/coolant and, thus, further decrease the ethylene glycol concentration in liquid mixture to be recycled. Further, the spent antifreeze/coolant is typically characterized as containing at least one heavy metal selected from the group consisting of lead, iron, zinc, manganese, copper, molybdenum, and aluminum and various organic oils from the internal combustion engine or present as a result of contamination after removal of the antifreeze/coolant.

The antifreeze/coolant will also typically contain one or more organic compounds other than the polyhydric alcohol(s) component. Such organic compounds may be present as a result addition as a functional additive to the original antifreeze/coolant or may be present as a degradation product of the polyhydric alcohol, e.g., ethylene glycol, or other organic compound present in the original antifreeze/coolant. For example, it is well known that under the working conditions that an antifreeze/coolant experiences in an automotive cooling system that thermal degradation of ethylene glycol and other organic compounds present in the working antifreeze/coolant will result in the presence of organic degradation products. Typical organic degradation products of ethylene glycol include, but are not limited to, formic acid, glycolic acid and acetic acid. Antifreeze/coolants also are known to contain inorganic components as corrosion inhibitors including, but not limited to, silicate, nitrate, nitrite, silicone compounds, phosphate, chloride, sulfate, carbonate and mixtures thereof, and salts commonly found in water.

PROFILE OF USED ANTIFREEZE/COOLANT FROM COOLING SYSTEMS

The importance of understanding the chemical make-up of the used antifreeze/coolant to be recycled is important, since in general the recycle process will treat used antifreeze/coolant taken from several cooling systems and mixed to form a larger volume of used antifreeze/coolant for treatment. Accordingly, for example, recycle processes will in general be treating a used antifreeze/coolant which is typically the average of 20 to 30 cooling systems as a result of mixing used antifreeze/coolant on a single collection container. As a result, there is a similarity in the used antifreeze/coolant employed as the starting used antifreeze/coolant for most recycle processes as a result of this "average" profile which results from mixing used antifreeze/coolant.

Analyses of spent antifreeze/coolants taken from commercial antifreeze/coolant change-over facilities (including flushing liquids, e.g., water), are set forth in Table A:

TABLE A

| Component[2] | Low Value[3] | High Value[3] | Average Value[1,3] |
|---|---|---|---|
| pH | 8.5 | 10.0 | 9.3 |
| Wt. % EG | 12.1 | 40.0 | 28.8 |
| Wt. % DEG | 0.5 | 3.5 | 1.37 |
| Wt. % PG | ND | 2.02 | 0.96 |
| TSS | 64 | 1846 | 544 |
| $NO_2$ | 10 | 50 | 15 |
| $NO_3$ | 56 | 740 | 469 |
| P | 125 | 730 | 438 |
| Cl | 1 | 31 | 18.5 |
| F | ND | 9 | 5 |
| Sulfate | 22 | 169 | 100 |
| B | 67 | 258 | 164.4 |
| Cu | 2.0 | 15.9 | 6.1 |
| Fe | 7.6 | 583 | 82.5 |
| Al | 1.8 | 71.3 | 13.7 |
| Pb | 1.5 | 136 | 25.6 |
| Ca | 1.5 | 34.1 | 9.13 |
| K | 234 | 1406 | 745 |
| Mg | 0.9 | 19.9 | 5.9 |
| Mo | 3.6 | 56.8 | 17.8 |
| Na | 676 | 2074 | 1420 |
| Si | 40.8 | 269.1 | 126.8 |
| Sn | 0.9 | 24.7 | 11.8 |
| Zn | 1.1 | 27.6 | 5.8 |
| TTZ | 130 | 370 | 242.7 |
| Acetate | 12 | 219 | 48.9 |
| Glycolate | 121 | 858 | 503 |
| Formate | 2 | 241 | 129 |
| Benzoate | 10 | 2590 | 385 |
| EDTA | 40 | 64 | 46 |
| Oil | ND | 1.0 | 0.03 |

[1] Low, High and Average Values (in ppm except where shown as wt. %) are based upon thirty (30), 55 gallon antifreeze/coolant samples taken from collection tanks at commercial antifreeze/coolant businesses in the United States of America.
[2] Abbreviations have the following meaning: WT. % = Weight Percent; EG = Ethylene Glycol; DEG = Diethylene Glycol; PG = Propylene Glycol; $NO_2$ = Nitrite; $NO_3$ = Nitrate; Cl = Chloride; F = Fluoride; P = Phosphorus; B = Boron; Cu = Copper; Fe = Iron; Al = Aluminum; Pb = Lead; TTZ = Tolyltriazole; EDTA = Ethylene Diamine Tetracetic Acid; and Oil = weight percent oil as an insoluble organic phase; TSS = Total Suspended Solids (ppm; gravimetric analysis with 0.45 micron filter); and ND = below detection limit of 2 ppm. Other elements by their Chemical Symbols.
[3] Concentrations are in parts per million (ppm). All components are given as total of soluble and insoluble forms.

PROCESSES FOR TREATING SPENT ANTIFREEZE/COOLANT

I. One process useful in providing a recycled antifreeze/coolant is disclosed in copending U.S. Ser. No. 07/564,262, filed Aug. 8, 1990, entitled, "PROCESS FOR TREATMENT OF AQUEOUS SOLUTIONS OF POLYHYDRIC ALCOHOLS" incorporated herein in its entirety by reference. The recycle process of U.S. Ser. No. 07/564,262 comprises taking used antifreeze/coolant from the cooling system of an internal combustion engine which contains between about 5 weight percent and about 95 weight percent polyhydric alcohol, generally between about 30 to 70 weight percent ethylene glycol, which contains at least one heavy metal and typically containing an oil component. This recycle process generally comprises the steps of:

(i) adjusting the pH of said polyhydric alcohol-containing composition to between about 4.0 and about 7.5 by addition of an effective amount of an pH adjusting agent to form a pH-adjusted composition; and (ii) adding an effective amount of a precipitating agent for at least one heavy metal and/or oil component present in the pH-adjusted composition.

In addition to the above steps the recycle process of U.S. Ser. No. 07/564,262 also may include one or more of the following steps:

(iii) preferably also includes adding to the pH-adjusted composition of step (ii) an effective amount of a coagulating agent and an effective amount of a flocculating agent effective in forming a precipitate containing at least one heavy metal;

(iv) passing the pH-adjusted composition through a first filtration means to remove a major amount of said heavy metal-containing precipitate;

(v) passing the pH-adjusted composition after the first filtration means through an organic separation means effective in removing organic compounds (other than the polyhydric alcohol(s)) from the pH-adjusted composition;

(vi) passing the pH-adjusted composition from the first filtration means through a second filtration means effective in the physical separation of particles of a smaller size that said first filtration means;

(vii) passing said pH-adjusted composition through a third filtration means having an effective physical separation of particles by size smaller than said second filtration means; and (viii) passing said pH-adjusted composition after filtration through an ion exchanger (anion and/or cation) effective in the removal of at least one solubilized heavy metal from said pH-adjusted composition.

Prior to addition of the precipitating agent the pH of the spent antifreeze/coolant is adjusted by addition of an effective pH-adjusting agent to adjust the effective pH to improve the precipitation of heavy metal(s) and is preferably adjusted to a pH between about 4.0 and about 7.5 and more preferably between about 4.5 and 7.0. This pH adjustment improves the precipitation of heavy metals present in the spent antifreeze/coolant while concurrently adjusting the pH at a sufficiently high pH so as to minimize acidic solubilization of heavy metal compounds. The pH-adjusting agent may be any organic or inorganic compound which effectively adjusts the pH to the selected pH, although it has been unexpectedly found that the use of nitric acid as the pH-adjusting agent in conjunction with the use of aluminum nitrate as the precipitating agent provides unexpected results for precipitating both solubilized and insoluble lead species and for removing oil components present in spent antifreeze/coolant from the cooling systems of internal combustion engines. Organic acids, acidic organic salts, inorganic acids and acidic inorganic salts are employable herein being effective in adjusting the pH of the antifreeze/coolant. Representative acids include nitric acid, phosphoric acid, sulfuric acid, hydrochloric acid, carboxylic acids, mixtures thereof and the like. It has been observed that salts useful as both pH-adjusting agents and/or precipitating agents include the following representative acidic salts: the chlorides and nitrate salts of calcium, magnesium, zinc, aluminum and iron; the sulfate salts of magnesium, zinc, aluminum and iron; and the like. It is beneficial to employ nitric acid as the pH-adjusting agent so as to prevent the introduction of corrosive anions and/or anions which may interfere with precipitation of heavy metals present in the spent antifreeze/coolant during the pH adjustment step, although the concurrent adjustment of pH and precipitation of heavy metal(s) with an acidic salt, e.g., preferably an aluminum nitrate hydrate such as $Al(NO_3)_3 \cdot 9H_2O$, is within the scope of the instant invention.

The precipitating agent may be selected to provide for the formation of heavy metal(s) precipitate in the pH-adjusted antifreeze/coolant. The precipitating agent need not result in the actual formation of a solid precipitate if a coagulant and/or flocculant are to be employed but only need render heavy metal(s) and/or oil present in the spent antifreeze/coolant susceptible to precipitation in the presence of coagulant and flocculant. When the precipitating agent is employed without the use of a coagulant and/or flocculant, it has been observed that the rate of formation and separation of the precipitate may be too slow for effective commercial use of the process, although the benefits of instant process will nonetheless be achieved. The precipitating agent is added in an effective amount to precipitate a selected amount of heavy metal(s) present in the spent antifreeze/coolant. As aforementioned, the heavy metals most commonly found in spent antifreeze/coolant are lead (Pb from lead solder corrosion), iron (Fe from water and radiator corrosion), zinc (Zn from metal corrosion and from zinc salts employed in antifreeze/coolants), copper (from radiator corrosion) and aluminum from corrosion (water pump, radiator, engine head and engine block). It has been observed that the concentrations of solubilized lead and iron in a spent antifreeze/coolant are on the order of up to about 100 parts per million (ppm) lead, and up to about 25 ppm iron, respectively. It has also been observed that insoluble lead components may be present in concentrations up to about 150 ppm and insoluble iron components may be present in concentrations up to about 600 ppm. Typically total concentrations of lead and iron are set forth in Table A, hereinbefore. The effective amount of precipitating agent for such concentrations of Pb and Fe will typically be between about 100 ppm and about 6000 ppm (based upon use of $Al(NO_3)_3 \cdot 9H_2O$ as the precipitating agent) and preferably between about 500 ppm and about 5000 ppm. The effective amount of precipitating agent employed is related to the equivalents of heavy metal(s) to be precipitated and will vary depending upon the equivalents of the selected precipitating agents useful herein for forming heavy metal precipitates.

As aforementioned, selection of the precipitating agent may be from that group of organic and/or inorganic compounds effective in the formation of a substantially insoluble species of at least one heavy metal present in the spent antifreeze/coolant at the adjusted pH and may include salts of heavy metal(s) such as phosphates, chlorides, sulfates, oxalates and the like. The term "substantially insoluble" is meant to refer to a heavy metal species which will form as one or more precipitable species at a pH between about pH 4.0 and pH 7.5. Surprisingly, it has been found that use of aluminum nitrate $(Al(NO_3)_3.9H_2O)$ as a precipitating agent for lead after pH adjustment (to between about 4.0 and about 7.5) of the antifreeze/coolant with nitric acid (as the pH-adjusting agent) is particularly advantageous for use in formation of a lead precipitate and is also most beneficial for use in forming a precipitation with the additional use of a coagulant and/or flocculant. The exact mechanism by which aluminum nitrate beneficially provides for formation of a precipitate of lead is not fully understood but may relate to chemical reaction with lead and/or may involve physical adsorption of lead species on the surface of aluminum hydroxide or an aluminum oxide or other aluminum species formed in situ by addition of aluminum nitrate.

The selection of the coagulant and flocculant is correlated to the alcohol-based antifreeze/coolant being treated and is made to provide for effective precipitation and filtration of the precipitate and separation of the precipitate by a mechanical filter. The coagulant may be any of the well known commercially available coagulants including Calgon 2466, Cyanamid 572C, mixtures thereof and the like. The flocculant may be any of the well known commercially available flocculants including PRIMAFLOC® C-3, MAGNIFLOC® 572C, Calgon 7736, Cyanamid 1820A, mixtures thereof and the like. Calgon POL-E-Z® 2466 is a high molecular weight, high charge cationic polyelectrolyte available from Calgon Corporation. PRIMAFLOC® C-3 is a cationic polyelectrolyte flocculant characterized as a water-soluble polyamine (29–31%) and is available from Rohm and Haas Company. Calgon POL-E-Z® 7736 is a high molecular weight, anionic polyelectrolyte available from Calgon Corporation. MAGNIFLOC® 572C (flocculant) is a very low molecular weight, liquid cationic flocculant available from American Cyanamid Company. Cyanamid 1820A is a cationic flocculant available from American Cyanamid Company. The selection of coagulants and flocculants for precipitating solids in water based systems is well known as evidenced by the discussion in "The Nalco Water Handbook" Second Edition, (ISBM 0-07-045872-3), 1988, at Part 2, Chapter 8 at pages 8.3 to 8.23, incorporated herein by reference.

In one embodiment of the recycle process of U.S. Ser. No. 07/564,262 the antifreeze/coolant is a spent antifreeze/coolant from the cooling system of an internal combustion engine, typically from an automobile or truck, having its pH adjusted to between about 4.5 and about 7.0 with nitric acid as the pH-adjusting agent, followed by treatment with an effective amount of aluminum nitrate as the precipitating agent, followed by addition of coagulant, preferably Calgon 2466, and flocculant, preferably Calgon 7736. The effective amount of coagulant is typically between about 75 ppm and about 300 ppm, preferably between about 150 ppm and about 225 ppm. The effective amount of flocculant is typically between about 25 ppm and about 300 ppm and preferably between about 50 ppm and about 100 ppm. It has been observed that there is an effective concentration range of coagulant and flocculant in the coagulant and flocculant solutions when such are to be added to the antifreeze coolant after such has been treated with the pH-adjusting agent and the precipitating agent. Surprisingly, it has been found that commercially available coagulants and flocculants are sold at concentrations significantly greater than beneficially suitable for use in the instant process. For example, when treatment of a lead-containing automotive antifreeze/coolant is effected with Calgon 2466 as the coagulant and Calgon 7736 as the flocculant after the antifreeze/coolant has been treated with effective amounts of nitric acid and aluminum nitrate, it has been observed that the coagulant and flocculant as commercially available should be beneficially diluted from its original commercial concentration by the addition of water or other suitable solvent. For example, suitable dilution of coagulant Calgon 2466 and flocculant Calgon 7736 for use in the instant invention may be prepared by mixing 100 parts (by weight or by volume) of the coagulant or the flocculant with water to form up to 40,000 parts of coagulant or flocculant solution for use in the instant invention. The aforementioned water diluted mixtures will preferably result in effective concentrations of coagulant or flocculant in the resulting diluted water mixtures wherein the concentration of coagulant or flocculant is 0.25% to 5.0% of the concentration of the original commercial concentration of the coagulant or flocculant. Although the exact reason for the beneficial effect obtained by use of a diluted coagulant or flocculant and the beneficial correlation of the concentration of the coagulant and flocculant to the antifreeze/coolant is not fully understood it has been observed that such may be related to the unique chemical environment resulting from the use of an originally formulated ethylene-glycol based antifreeze/coolant in the cooling system of an internal combustion engine and from localized concentrations of coagulant or flocculant resulting from the inherent difficulty in mixing large volumes of liquids. The actual correlation in the concentration is believed to result in an effective concentration of coagulant and flocculant, as described above based upon the range of the heavy metals observed to be present in antifreeze/coolant removed from automotive cooling systems.

The antifreeze/coolant will form a solids phase (precipitate) and a liquid phase after treatment with the pH-adjusting agent and precipitating agent and in a further embodiment preferably treatment as to coagulant and flocculant, as described above. The precipitate may be removed by mechanical filtration. In addition, it has been observed that proper agitation of the treated antifreeze/coolant enables skimming of precipitate from the top of the treated antifreeze/coolant as some portion of the precipitate is present at the surface of the treated antifreeze/coolant. Further, it has been observed that recirculation of the spent antifreeze/coolant in the mixing tank by introduction of the recirculated stream above the surface of the antifreeze/coolant in the mixing tank is beneficial in forming a precipitate suitable for skimming as compared to the form of the precipitate formed when the recirculated stream is introduced below the surface of the antifreeze/coolant in the mixing tank. Accordingly, it is preferred to have a recirculation of the spent antifreeze/coolant in the mixing tank from below the surface of the antifreeze/coolant in mixing tank to a position sufficiently above the surface so as to expose the recirculated antifreeze/coolant to air whereby some degree of contact with air occurs, such having been observed as effective in improving the form of the precipitate for skimming. This preferred recirculation is preferably commenced prior to the addition of the pH adjusting agent and precipitating agent. It has been observed that the use of a process step wherein skimming of the surface of the treated antifreeze/coolant is employed is beneficial in reducing the amount of precipitate which must be removed by filtration. This reduction in the amount of precipitate to be removed by filtration both increases the rate at which the treatment process may be carried out and increases the useful life of the filtration means, thus decreasing the number of times the filtration means must be replaced. The effective particle size removed by the filtration means will depend in part on whether a single or multiple filtration steps are to be employed. If a single filtration step is to be employed the filtering means will preferably remove particles having a particle size greater than about 50 microns, although use of a single filtration step is not employed. If this first filtration is the first filtration means in a series of filtration means, then this first filtration means will preferably be effective in the removal of particles having a particle size greater than about 100 microns. In one embodiment it has been found to be beneficial to employ at least three filtration steps wherein the first filtration means is effective in removing species larger than about 100 microns, a second filtration means effective in removing species larger than about 40 microns and a third filtration means is beneficially employed wherein such is effective in removing species larger than about 5 microns. An optimal fourth filter may be employed wherein such fourth filtration means is effective in removing species larger than about 0.2 microns, preferably larger than about 0.1 microns. Mechanical filtration means having effective filtration sizes as above discussed are well known in the prior art. Optionally, as herein described, an organic separation filter may be provided in conjunction with the previously discussed mechanical filters.

In a further embodiment, the treated, filtered, spent antifreeze/coolant is passed through an active filter for the removal of organic compounds, e.g., oils, aldehydes and organic acids. Representative of such active filters are the various activated carbon filters sold under the trade name Fulflo# by Parker Hannifin Corporation-Commercial Filters Group or a No. 2 Anthacite filter sold by Penfield Liquid Treatment. The Fulflo# filter is characterized by its honeycomb filter structure having an activated carbon surface while the Penfield filter is a loosely packed carbon filter. The active carbon filter acts as an organic separation means effective in the selective removal of organic compounds from the polyhydric alcohol/water mixture forming spent antifreeze/coolant.

It has been found beneficial to provide two or more filtration means for the spent antifreeze/coolant (either before or after aforementioned organic separation means) to effectively remove materials greater than about 5 microns, and more preferably to remove materials greater than about 0.2 microns. It has been found that the use of one or more additional mechanical filtration steps in conjunction with a first filtration means step is most advantageous in the separation of bulky organic and inorganic compounds and both large and small particulate solids. Further, by providing a series of ever smaller size filters the likelihood of clogging smaller pore filters with larger materials is effectively eliminated. In one embodiment the process employs a first filtration means effective in removing materials greater than about 100 microns, a second filtration means effective in removing materials greater than about 40 microns, a third filtration means effective in removing materials greater than about 5 microns, and a fourth filtration means effective in removing materials greater than about 0.2 microns.

In a further embodiment the instant process may also involve treatment with at least one ion-exchange resin to remove solubilized species present in the spent antifreeze/coolant. A possible result of the initial pH-adjustment of the instant process is the formation of solubilized cationic and/or anionic species of one or more heavy metals. The pH-adjustment to a pH between about 4.0 and about 7.5 is selected so to minimize the formation of such solubilized cationic and/or anionic species of such heavy metals, especially solubilized lead species. Although it has been observed that no such solubilized cationic species (less than the lowest measurement limit of 2 ppm), e.g., solubilized lead, are present after the addition of the pH-adjustment agent, precipitating agent, coagulant and flocculant it is believed to be beneficial to treat the filtered, spent antifreeze/coolant with a cation and/or anion exchange resin to assure that essentially no solubilized heavy metal is present. It has also been observed that such ion exchangers also may act as filtration means for effectively removing materials having a size greater than about 2.0 microns. Further, since some solubilized species will pass through filtration means having a pore size greater than 0,005 and remain as solubilized species it is beneficial to employ an ion exchange material whereby such species are selectively removed by other than physical separation.

It is desirable to remove any solubilized heavy metals from the spent antifreeze/coolant so that such may be properly handled and properly disposed. Accordingly, the filtered, spent antifreeze/coolant may be treated with a cation exchange and/or anion exchange resin effective in the removal of solubilized heavy metal cation(s), or anions. Cation exchange resins useful in the removal of solubilized heavy metal cations include well known cation exchange resins such as Rohm and Haas DP-1, Rohm and Haas Amberlite ® IRC-718, Duolite ® C-464, Purolite ® C-106 and Ionic ® CNN. Rohm and Haas Amberlite ® IRC 718 is preferred owing to its effectiveness in the removal of solubilized lead and its cost. Amberlite ® IRC 718 is a chelating cation exchange resin having a high affinity for heavy metal cations over alkali or alkaline earth metals in the pH range between about 4.0 and about 7.5 and is formed from Dow Chemical Company's SBR resin; a styrene-divinyl benzene material and is available from Rohm and Haas. Anion exchange resins which may be employed herein include Rohm and Hass Amberlite ® IRA 400; Purolite ® A-600; Ionic ® ASB-1; and Duolite ® A-109. It has been observed that the use of an anion exchange resin may not always be beneficial owing to the high concentration of anions present, present in the treated antifreeze/coolant, e.g., nitrate, in the treated antifreeze. Nevertheless, there may be instances where an anion exchange resin may be beneficially employed, e.g., where the anion exchange resin is selective to one or more anionic species. Further, it is well known that ion exchange resins having both cation and anion exchange characteristics are commercially available and such dual exchange resins may be employed herein. For example the non-exchange media of U.S. Pat. No. 4,908,137, incorporated herein, is believed to be a novel non-exchange media useful herein in the removal of heavy metal ions.

The treatment with the cation and/or anion exchange resin ("ion exchange") may be accomplished after suitable mechanical filtration of the spent antifreeze/coolant after the addition of the pH-adjusting agent, precipitating agent, coagulant and flocculant has resulted in precipitation of insoluble heavy metal compounds. Since the presence of large particulate matter will tend to clog most ion exchange materials, it is preferred that the ion exchange step follow a mechanical filtration step where particles having a size greater than about 5 microns have been removed.

The reference to "filtration means" is meant to designate the various filtration devices hereto known in the prior art for use in the physical separation of materials (including both organic species and inorganic species) based on size. Filtration devices suitable for use in the instant invention are commercially available. For example, the first filtration means of 100 microns and above may be a 3M Brand liquid filter bag formed from polypropylene or stainless steel as described in 3M sales brochure 70-0701-3209-0(201)iii 1989, incorporated herein. The second filtration means having separation means of about 40 microns and above may be a 3M Brand liquid cartridge filter having a pleated polypropylene design as described in 3M sales brochure 70-0702-2790-8(201.5)11, incorporated herein.

In one embodiment the treatment with a cation exchange resin may be replaced in part or in whole with treatment with an anion exchange resin. In some instances the heavy metal(s) may be present or may be converted into an anionic species. In some instances it may be beneficial to treat the spent antifreeze/coolant to form an anionic species of the heavy metal, since in some instances its removal as an anionic species may be more effective than its removal as a cationic species. The formation of such anionic species may be beneficial owing to the desire to increase the reserve alkalinity of the spent antifreeze/coolant in preparation for its reprocessing into a working antifreeze/coolant for use in an automotive cooling system.

The final composition obtained from the various embodiments of the instant invention are characterized as having lower concentrations of one or more heavy metal components and is typically characterized as being an aqueous composition(s) containing between about 5 and about 95 weight percent polyhydric alcohol, preferably ethylene glycol, and containing less than about 5 ppm soluble lead, generally less than 2 ppm soluble lead. These aqueous polyhydric alcohol compositions may be employed in the manufacture of a working antifreeze by addition of corrosion inhibitors hereto employed in the manufacture of antifreeze/coolant compositions or may be employed for other common uses for the polyhydric alcohol.

When the use is for antifreeze/coolant, such corrosion inhibitors will be employed in effective amounts correlated to any residual concentration of components of corrosion inhibitors present from that present in the spent antifreeze/coolant which was not removed by the instant process. For example, solubilized silica and nitrate may be present in the compositions derived from the instant process, since the various steps of precipitation, organics separation and mechanical filtration may not be effective in their complete removal. Chemical analysis of the treated spent antifreeze/coolant will provide a basis for correlating the effective amount of corrosion inhibitor which should be added to the treated aqueous antifreeze/coolant to form an effective working antifreeze. In some instances the formation of a working antifreeze may also require the addition of ethylene glycol or fresh antifreeze or removal of water to obtain a solution having the desired freezing point. Removal of water from the aqueous ethylene glycol may be by distillation, extraction or other known separation means.

The various steps of the recycle process of U.S. Ser. No. 07/564,262 may be carried out at an effective temperature wherein the antifreeze/coolant is in a liquid state and is preferably between about 18° C. to about 45° C. and at an effective pressure, preferably between about 0.9 atm to about 1.1 atm, or such other temperatures or pressures as may improve the process.

It has been observed that it is not preferred to pass the precipitate formed by addition of the pH-adjusting agent, precipitating agent, coagulant and flocculant through a high shear mechanical pump, since a high shear mechanical pump tends to form particles of smaller size by mechanical shearing, thus making it more difficult to remove particles with large size filters. Accordingly, it has been found that it is preferred to place a pumping means after the first filtration step which to provide a pulling action after the first filtration means or alternatively, provide a diaphragm or other low shearing type pump ahead of first filtration means. Representative of high shear pumps is a MOYNO ® SP Pump (available from Robbins & Wyers, Inc.) and representative of a low shear pump is a Twin Diaphragm Pump (available from the ARO Corporation). It has also been observed that by employing skimming of precipitate from the surface of antifreeze/coolant in the vessel to which the pH-adjusting agent, precipitating agent, flocculant and coagulant are added that sufficient precipitate can be removed to significantly reduce the problems associated with high shear pumps.

The recycle process of U.S. Ser. No. 07/564,262 may be carried out in a batch wise or, alternatively, in a continuous mode. When carried out in a batch mode, the process is conducted by placing a selected quantity of spent antifreeze/coolant in a vessel. The pH-adjusting agent and precipitating agent are added followed by addition of the coagulant and flocculant whereby a precipitate will be formed. The contents of the vessel are then filtered by a first filtration means to remove the precipitate from the liquid phase. It has been found advantageous to minimize the mechanical action on the precipitate during this first filtration step so as to minimize the fraction of smaller size particles which form as a result of mechanical abrasion. Such mechanical abrasion may be minimized by manual mixing for about 5 minutes after all ingredients have been added during which time it may be advantageous to skim precipitate from the surface of the mixture. The pH-adjusted composition may then be sequentially passed through one or more filtration means, organic separation means, additional filtration means and ion exchange means.

The treated antifreeze/coolant may be suitable for use as a component of a working antifreeze/coolant without further treatment or may be distilled to remove water and/or organic component and, thus, provide a higher content polyhydric alcohol solution. Alternately, the instant process is well suited to be carried out in a continuous manner based upon the process steps employed in the batchwise process discussed above.

The recycle process of U.S. Ser. No. 07/564,262 may also be employed as a continuous recycle process in an antifreeze/coolant change-over process where the treated antifreeze/coolant is returned to the cooling system of an internal combustion engine after the addition of inhibitors and other suitable chemicals. Processes wherein a treated antifreeze/coolant is reintroduced to an engine cooling system include U.S. Pat. Nos. 4,149,574, Re. 31,274, 4,791,890 and 4,792,403; said patents incorporated herein by reference. For example, in U.S. Pat. No. 4,793,403 the instant process may be substituted for the second means for treating the removed coolant (see: column 3, line 11 to column 3, line 28). In one embodiment the instant process is employed as the intermediate treatment step in the process of copending U.S. Ser. No. 200,347, filed May 31, 1988, entitled, "FLUSH AND FILL METHOD AND APPARATUS" incorporated herein by reference thereto.

II. Recycle processes such as that disclosed in U.S. Pat. No. 4,946,595, entitled "PROCESS AND APPARATUS FOR RECYCLING ENGINE COOLANT" (incorporated herein in its entirety by reference thereto) may be employed as the recycle process from which a recycled, used antifreeze coolant may be obtained for reinhibition according to the instant invention.

Several alternative recycling processes have been discussed in the prior art and are commercially available. These recycle processes include: 1) ultrafiltration; 2) chemical filtration; 3) chemical filtration with precipitation, oxidation and ionization; 4) chemical filtration with ionization; 5) vacuum distillation; 6) filtration with ion exchange; 7) filtration with centrifuge and 8) reverse osmosis. The common element to such commercial recycle processes is that the recycled antifreeze/coolant has a chemical fingerprint which is different from virgin ethylene glycol. This chemical fingerprint is derived from the use history of the antifreeze/coolant, i.e., its use in a cooling system and the chemical components contained therein as a result of this use, and the recycle process employed to treat the antifreeze/coolant after use in a cooling system.

REINHIBITOR PACKAGE AND MANUFACTURING PROCESS FOR REINHIBITED, RECYCLED ANTIFREEZE/COOLANT

The following "reinhibitor packages" have been found to be effective in providing effective corrosion inhibiting protection to the metal components of automotive cooling systems (passed ASTM TEST METHODS D-1384-87 and D-4340-89, as discussed hereinafter) when added to recycled used antifreeze/coolant (Additive Package #1 being added prior to Additive Package #2) obtained from several different recycle processes according to the instant invention. The concentrations of the components in the reinhibitor package were correlated to the chemical fingerprint of the recycled used antifreeze/component by adding effective amounts of corrosion inhibitors and buffers to provide a reinhibited, recycled used antifreeze/coolant with the preselected corrosion inhibiting properties for automotive cooling systems (Reinhibitors A to E) and for a heavy duty truck (reinhibitor C, D and E, as shown). When the system is an automotive or heavy duty truck cooling system representative chemical fingerprint components to consider for the correlation are the concentrations of buffering agents, (borate, phosphate, etc.), ethylene glycol content, silicate, corrosion inhibitors (e.g., molybdate, azoles, etc.) reserve alkalinity and pH. The concentration of these chemical components in the recycled, used antifreeze/coolant was correlated to the corresponding components in the reinhibitor package which is correlated to preselected effective corrosion inhibitor concentrations (for example General Motors Formula 6043 or were selected as the preselected concentrations) for the final antifreeze/coolant which then passed ASTM Test Methods D-1384-87 and D-4340-89 when evaluated. The following reinhibitor packages were employed according to the invention at the per gallon of recycled antifreeze/coolant amounts shown in parenthesis:

| Component | Wt. % | Component | Wt. % |
|---|---|---|---|
| REINHIBITOR A* | | | |
| ADDITIVE PACKAGE #2 | | ADDITIVE PACKAGE #1 | |
| Water | 54.43 | Sodium Silicate Grade 40 | 58.041 |
| Borax 20% in Ethylene Glycol | 15.24 | Sodium Hydroxide, 50% | 11.354 |
| Potassium Hydroxide, 45% | 18.42 | Water | 30.605 |
| Phosphoric Acid, 75% | 5.58 | (0.5 fl. oz./gal.) | |
| Sodium Tolyltriazole, 50% | 1.00 | | |
| Sodium Molybdate, 35% | 4.75 | | |
| Silicone | 0.58 | | |
| (6 fl. oz./gal.) | | | |

*Reinhibition for recycled, used antifreeze/coolant from process of U.S. Ser. No. 07/564,262.

| REINHIBITOR B* | | | |
|---|---|---|---|
| ADDITIVE PACKAGE #1 | | ADDITIVE PACKAGE #2 | |
| Ethylene Glycol | 45.0000 | Ethylene Glycol | 26.6342 |
| Water | 26.2331 | Water | 36.2484 |
| Sodium Hydroxide, 50% | 13.3155 | Borax, 20% in Ethylene Glycol | 22.9573 |
| Sodium Mercaptobenzothiazole, 50% | 9.3704 | Sodium Molybdate, 35% | 8.6895 |
| | | Sodium Tolyltriazole, 50% | 2.4026 |
| Silicone | 0.9938 | Phosphoric Acid, 75% | 3.0340 |
| Sodium Silicate (Grade 40) | 4.9323 | Uranine Dye, 40% | 0.0340 |
| Antifoam | 0.1139 | (4 fl. oz/gal.) | |
| Alizarine Dye | 0.0510 | | |
| (4 fl. oz./gal.) | | | |

*For addition to a recycle process (Reverse Osmosis) to provide a final antifreeze/coolant similar to General Motors formula 6043 for automotive cooling system.

| Component | Wt. % | Component | Wt. % |
|---|---|---|---|
| -continued | | | |
| REINHIBITOR C* | | | |
| ADDITIVE PACKAGE #1 | | ADDITIVE PACKAGE #2 | |
| Ethylene Glycol | 9.1383 | Borax, 20% in EG | 99.9660 |
| Water | 56.7889 | Uranine Dye, 40% | .0340 |
| Borax, 20% in Ethylene Glycol | 13.5771 | (6 fl. oz/gal.) | |
| Sodium Hydroxide, 50% | 7.6996 | | |
| Phosphoric Acid, 75% | 3.0340 | | |
| Sodium Tolyltriazole | 4.2002 | | |
| Silicone | 0.3256 | | |
| Sodium Silicate Grade 40 | 1.8895 | | |
| (6 fl. oz./gal.) | | | |

*For addition to a recycle process (Reverse Osmosis) to provide a final antifreeze/coolant similar to General Motors formula 6038 for a Heavy Duty, cooling system.

| REINHIBITOR D* | | | |
|---|---|---|---|
| ADDITIVE PACKAGE #1 | | ADDITIVE PACKAGE #2 | |
| Ethylene Glycol | 28.7986 | Water | 20.7099 |
| Water | 54.0478 | Borax, 20% in Ethylene Glycol | 76.5018 |
| Sodium Hydroxide, 50% | 12.2767 | Phosphoric Acid, 75% | 2.7543 |
| Sodium Tolyltriazole | 2.3986 | Uranine Dye, 40% | 0.0340 |
| Silicone | 0.3880 | (4 fl. oz/gal.) | |
| Sodium Silicate | 1.9256 | | |
| Antifoam | 0.1139 | | |
| Alizarine Dye | 0.0510 | | |
| (4 fl. oz./gal.) | | | |

*For addition to a recycle process (Reverse Osmosis) to provide a final antifreeze/coolant similar to General Motors formula 6038 for Heavy Duty, cooling system.

| REINHIBITOR E* | | | |
|---|---|---|---|
| ADDITIVE PACKAGE #1 AUTOMOTIVE | | ADDITIVE PACKAGE #2 AUTOMOTIVE/HEAVY DUTY | |
| Ethylene Glycol | 11.8396 | Ethylene Glycol | 28.4081 |
| Water | 54.8685 | Water | 43.0527 |
| Sodium Hydroxide, 50% | 9.2549 | Borax, 20% in Ethylene Glycol | 22.9573 |
| Sodium Molybdate, 35% | 8.6895 | Sodium Tolyltriazole, 50% | 2.4000 |
| Sodium Mercaptobenzothiazole, 50% | 9.3704 | Phosphoric Acid, 75% | 3.0340 |
| | | Antifoam | 0.1139 |
| Silicone | 0.9938 | Uranine Dye, 40% | 0.0340 |
| Sodium Silicate Grade 40 | 4.9323 | (4 fl. oz/gal.) | |
| Alizarine Dye | 0.0510 | | |
| (4 fl. oz./gal.) | | | |
| ADDITIVE PACKAGE #1 Heavy Duty | | | |
| Water | 31.7714 | | |
| Borax, 20% in Ethylene Glycol | 53.5445 | | |
| Sodium Hydroxide, 50% | 12.3195 | | |
| Silicone | 0.3880 | | |
| Sodium Silicate | 1.9256 | | |
| Alizarine Dye | 0.0510 | | |
| (4 fl. oz./gal.) | | | |

*For addition to a commercial process (Reverse Osmosis) to provide a final antifreeze/coolant similar to General Motors 6043 for automotive cooling systems and a final antifreeze/coolant similar to General Motors 6038 for Heavy Duty coolant systems in a manner that Additive Package #2 being common for both reinhibition packages.

The correlation of the chemical fingerprint of the recycled, used antifreeze/coolant to the concentrations of the chemical components in the reinhibited, recycled antifreeze/coolant will involve selection of the desired corrosion inhibition properties of the final antifreeze/coolant product. In general, the final antifreeze/coolant product will be reinhibited so as to provide an effective concentration of corrosion inhibitors for the selected cooling system of an internal combustion engine. Several tests for antifreeze/coolant have been developed to provide a standard by which the corrosion protection for an antifreeze/coolant is evaluated. Two well known tests are ASTM test methods, incorporated herein by reference:

| ASTM TEST METHOD | TITLE |
|---|---|
| D-1384-87[1] | Standard Test Method for Corrosion Test for Engine Coolants in Glassware |
| D-4340-89[2] | Standard Test Method for Corrosion of Cast Aluminum Alloys in Engine Coolants Under Heat-Rejecting Conditions |

[1] Current edition approved November 27, 1987. Published January 1988. Originally published as D-1384-55T. Last previous edition D-1384-80.
[2] Current edition approved March 31, 1989. Last previous edition D-4340-84.

In determining the effective corrosion inhibiting characteristics of the final reinhibited antifreeze/coolant for use in correlating the concentrations of the chemical components in the additive package of this invention to the chemical fingerprint of the recycled, used antifreeze/coolant the performance criteria of ASTM D-1384-87 or ASTM D-4340-89 may be selected as a basis for the correlation. The recycled, used antifreeze/coolants are characterized as having less than the effective corrosion inhibiting amount of at least one corrosion inhibiting agent which is desired to be in the final reinhibited, recycled antifreeze/coolant in an effective corrosion inhibiting amount to provide a preselected corrosion inhibition. Alternatively, the correlation may be made by employing preselected performance criteria based upon the preselected corrosion inhibition properties for the final product. For example, the desired effective corrosion inhibition properties of the final product may be selected as being less than that required by the aforementioned ASTM test methods owing to shortness of use or owing to differences as to whether the final product will be employed in a different cooling system (e.g., employed in an automotive cooling system or employed in a truck's cooling system where the corrosion inhibiting considerations are different owing to the different metals employed in the materials of construction of the different cooling systems). Another consideration in correlating the effective amounts of corrosion inhibitors in the recycled, used antifreeze/coolant is to consider the desired concentrations of chemical components in a well known antifreeze/coolant composition, such as General Motors Formula GM6043, and correlate the effective amounts of corrosion inhibitors contained therein to the chemical fingerprint of the recycled, used antifreeze/coolant.

The chemical components of commercial antifreeze/coolants are well known in the art as evidenced by the numerous patents discussed in the aforementioned section entitled "PROCESS FOR TREATING SPENT ANTIFREEZE/COOLANT". It is not within the scope of the instant invention to provide a new corrosion inhibition system for virgin ethylene glycol/water mixtures. Instead, the instant invention provides a process by which a recycled antifreeze/coolant (recycled after use in a cooling system of an internal combustion engine) may be employed to manufacture an antifreeze/coolant for reuse in a cooling system. Perhaps the easiest way to appreciate the instant invention is to understand the variability in the "chemical fingerprint" of recycled, used antifreeze/coolants which result from different recycle processes. The following chemical fingerprints were obtained from several commercial recycle processes:

| CHEMICAL COMPONENT | COMM. PROCESS[1,5] | U.S. Ser. No.[2,5] 07/564,262 | FPPF[3] | BG[4,5] |
|---|---|---|---|---|
| Phosphorus | 0 | 261 | 699 | 0 |
| Boron | 118 | 186 | 267 | 0 |
| Nitrate | 846 | 3500 | 780 | 0 |
| Silicon | 37 | 61 | 131 | 12 |
| TTZ | 178 | 114 | 402 | 0 |
| Molybdenum | 0 | 0 | 0 | 0 |

[1]Recycle process carried out using a commercial recycle process.
[2]Process carried out according to U.S. Ser. No. 07/564,262, filed August 8, 1990.
[3]Process carried out according to U.S. Pat. No. 4,946,595 without addition of corrosion inhibiting agents or buffering agents.
[4]Process carried out using a commercial recycle process available from BG Products, Inc., Wichita, Kansas (See: Radiator Reporter, October 1991, Volume 20, No. 10, RR 90-111).
[5]Recycled/coolants contained between about 38-55 weight percent water.

As is readily apparent from the above chemical fingerprints for the recycled used antifreeze/coolant from the four different recycle processes, there is a significant difference between the four processes as to the chemical fingerprint of the recycled, used antifreeze/coolant. Prior to the instant invention, the reinhibition of such recycled, used antifreeze/coolant was ad hoc and employed SCA ("Supplemental Codant Additive") reinhibition packages available for use with the heavy duty trucking business. Representative of this fact is the chemical additive employed in Example 1 of U.S. Pat. No. 4,946,595. The nitrite-containing chemical additive and the concentrations at which the chemical additive is employed are representative the SCA components employed as reinhibitor additives for heavy duty trucks. It is well known in the industry that nitrite-containing corrosion inhibitor packages are not currently employed for automotive cooling systems.

In one embodiment of the invention the correlation involves the concentration of at least one of phosphorus, boron, silicon, nitrate, Tolyltriazole ("TTZ") and molybdenum in the recycled, used antifreeze/coolant to the concentrations of such in the reinhibited, recycled used antifreeze/coolant to provide a preselected, effective corrosion inhibiting amount of corrosion inhibitors, for example, meeting the corrosion inhibition test of ASTM Test Method ASTM D1384-87 and/or ASTM Test Method D-4340-89. As noted previously, the correlation will take into account the chemical fingerprint of the recycled, used antifreeze/coolant wherein the particular chemical fingerprint is related to the particular recycle process employed. Specific correlations to the chemical fingerprint for a specific recycle process to the effective corrosion inhibiting properties are set forth in the examples.

In one embodiment the reinhibition package is added as two separate addition components with the first component containing a base stabilized silicate (e.g., sodium silicate) at a pH greater than 12 and the second component (at a pH below about 12) containing corrosion inhibitors stable at a pH below about pH 12 or buffering agents for buffering the final reinhibited, recycled antifreeze/coolant at a pH below about pH 12.

EXAMPLES

The following examples are provided to further illustrate the reinhibition package, manufacturing process and use provided by the instant invention and are not intended to be limiting thereof. As employed in the following examples the following abbreviations shall have the following meanings:

| | |
|---|---|
| Wt. %: | Weight Percent |
| EG: | Ethylene Glycol |
| DEG: | Diethylene Glycol |
| PG: | Propylene Glycol |
| TTZ: | Tolyltriazole |
| MBT | Mercaptobenzothiazole |
| $NO_3$: | Nitrate |
| $SO_4$: | Sulfate |
| F: | Fluoride |
| Cl: | Chloride |
| EDTA: | Ethylene Diamine Tetracetic Acid |
| TSS: | Total Suspended Solids (ppm; gravimetric analysis with 0.45 micron filter) |
| Oil: | Wt. % Oil as an insoluble organic phase. |
| Elements are referred to by their chemical symbols, e.g., Al is aluminum, Pb is lead, and etc. | |
| ml: | milliliter |
| ND: | None Detected at 2 ppm or higher. |
| ppm: | Parts per million. |
| Silicone: | Representative silicones are disclosed in U.S. Pat. No. 4,725,405 (incorporated herein by reference). |

The following examples include examples from U.S. Ser. No. 07/564,262, filed Aug. 8, 1990 so as to provide characterization of the recycled used antifreeze/coolants obtained from this process and examples in support of the instant invention. Examples 1, 2, and 3 have been taken in their entirety from U.S. Ser. No. 07/564,262. In examples 5 to 10/the sodium silicate is a base stabilized sodium silicate and each "Package A" has a pH of at least 12.0. The silicon value represents the silicon from silicate and silicone present in ratios as shown in U.S. Pat. No. 4,725,405 and, accordingly, silicone in examples 5 to 10 is reported in the silicon value with silicate.

EXAMPLE 1

A spent antifreeze/coolant was obtained from commercial antifreeze/coolant change-over facilities and was from the cooling systems of automotive and truck engines. The spent antifreeze/coolant was treated according to the instant invention using the following equipment in the order listed:
(1) Mixing Tank;
(2) ½" Diaphragm pump;
(3) 32" Bag Filter (3M 527A, 99.99 at 20 micron);
(4) 12" Bag Filter (McMaster Carr 5167K56, 100 micron);
(5) 20" Cartridge Filter (Pall RF400, 40 micron);
(6) 10" Activated Carbon (Filter Fulflo RC10, 10 micron);
(7) 20" Filter (3M 323A, 2 micron); and
(8) Cation Exchange Resin (Rohm and Haas Amberlite IRC-718).

A 5125 gallon sample of the spent antifreeze/cooling was placed in the mixing tank followed by the addition of 11.889 gallons of a 70 wt. percent nitric acid (remainder water). The contents of the mixing tank were then mixed by a mechanical mixer for 20 minutes. To this mixture was added 110.23 pounds of $Al(NO_3)_3.9H_2O$ powder. This mixture was mixed for 60 minutes. To this mixture was added 200 gallons of 0.5 weight percent coagulant Calgon 2466 and 66.7 gallons of 0.5 weight percent flocculant Calgon 7736. The resulting mixture was then mixed for eight hours and filtered using the above noted filters in the order listed.

Tables I and II show the analysis of the spent antifreeze/coolant both before and after treatment by the process of this invention. In Table I, the analysis of ethylene glycol, diethylene glycol and propylene glycol was conducted by standard refractive index and gas chromotographic methods, the oil percent was conducted by a gas chromotography, the total suspended solids were conducted by gravimetric analysis and all other analyses were conducted by High Pressure Liquid Chromatography ("HPLC") analysis or Ion Chromatography ("IC"). Table II shows the results of ICP analyses of several metals in their soluble and insoluble forms both before treatment and after treatment according to the instant invention. In addition, the precipitate collected by the first 100 micron filter bag was analyzed. Table I and Table II demonstrate the effectiveness of the instant process in removing heavy metals, particularly lead, iron, copper, aluminum, magnesium, zinc and oil from spent antifreeze/coolant compositions. Referring to Table I, it is shown that in one embodiment of the instant process that after treatment the concentrations of TTZ, BZT, oil, benzoate, glycolate and total suspended solids ("TSS") have been reduced. Referring to Table II, it is shown that after treatment the soluble forms of aluminum, boron, calcium, iron, potassium, magnesium, molybdenum, phosphorus, lead, silicon and zinc are reduced. The insoluble forms of aluminum, boron, iron, magnesium, molybdenum, phosphorus, lead and zinc were reduced.

It is particularly important to note that after treatment according to the invention that no soluble or insoluble lead was present in the antifreeze/coolant down to the detection limits of ICP analysis (about 2 ppm) and, accordingly, is consistent with current and presently proposed regulations of the Environmental Protection Agency as being a non-hazardous material. Further, it has been observed that the form of the heavy metals in the precipitate is such that the heavy metals are not leachable by water. Further, the precipitate contains various useful metal components and may be recycled for use as a component in cements, concrete, or used in other metal layered areas.

TABLE I

ANTIFREEZE/COOLANT COMPOSITION BEFORE AND AFTER CHEMICAL TREATMENT

| Analysis | Before Treatment | After Treatment |
|---|---|---|
| pH | 8.3 | 6.39 |
| EG, Wt % | 53.0 | 48.1 |
| DEG, Wt % | 2.0 | 1.9 |
| PG, Wt % | 0.33 | 0.34 |
| TTZ, ppm | 908 | 258 |
| BZT, ppm | 114 | ND |
| $NO_2$, ppm | 92 | 115 |
| $NO_3$, ppm | 1029 | 4166 |
| Benzoate | 3520 | 2896 |
| Oil, % | 0.5 | ND |
| F, ppm | 180 | 1.41 |
| Cl, ppm | 137 | 141 |
| $SO_4$, ppm | 290 | 259 |
| Acetate | 55 | 66 |
| Glycolate | 820 | 660 |
| Formate | 199 | 197 |
| Any acid, % | 0.05 | 0.04 |
| TSS, ppm | 509 | 19.0 |

TABLE II[1,2]

ANTIFREEZE/COOLANT COMPOSITION BEFORE AND AFTER CHEMICAL TREATMENT

| ELEMENT NAME | SOLUBLE FORM | | INSOLUBLE FORM | | PRE-CIPITATE |
|---|---|---|---|---|---|
| | Before | After | Before | After | |
| Al | 2.6 | ND | 6.1 | ND | 1340 |
| B | 434.8 | 303.6 | 23.7 | 3.2 | 1493 |
| Ca | 14.7 | ND | 6.7 | ND | 100.1 |
| Fe | 2.4 | ND | 23.6 | ND | 32.6 |
| K | 1206 | 986.6 | ND | ND | 789.5 |
| Mg | 8.1 | ND | 3.0 | ND | 30.6 |
| Mo | 48.5 | 20.5 | ND | ND | ND |
| Na | 2811 | 2308 | 65.0 | 30.9 | 2110 |
| P | 646.1 | 240.8 | 24.9 | ND | 95.8 |
| Pb | 3.0 | ND | 10.2 | ND | 11.5[3] |
| Si | 66.5 | 31.4 | 5.3 | ND | 15200 |
| Zn | 5.6 | ND | 5.4 | ND | 5.0 |

[1]Concentration in parts per million (ppm);
[2]ND means not detected at 2 ppm or higher
[3]EP Toxicity Testing (extractable lead) results were less than 0.1 ppm.

EXAMPLE 2

Treatment of a spent antifreeze/coolant obtained from the cooling systems of automotive and truck engines was treated according to the instant invention using the following combination of equipment in the order listed:
(1) 30 gallon tank;
(2) ½" Diaphragm air pump;
(3) 12" 50 micron Bag Filter (McMaster Carr No. 5167K56);
(4) 20" 40 micron Cartridge (Pall No. RF400);
(5) 10" 10 micron Carbon Filter (Fulflo No. RC10);
(6) 20", 5 micron Cartridge Filter (Pall RF050); and (7) 1.8 liter Cation Exchange Resin (Rohm and Haas Amberlite No. IRC-718)

A 10 gallon sample of a spent antifreeze/coolant was placed in the 30 gallon mixing tank followed by the addition of 60 ml of 70 weight percent nitric acid (remainder water). To this mixture was added 0.24 pounds of Al(NO$_3$)$_3$-9H$_2$O powder. This mixture was mixed for 15 minutes. To this mixture was added 1135.5 ml of 0.5 weight percent coagulant Calgon 2466 and 378.5 ml 0.5 weight percent of flocculant Calgon 7736. The resulting mixture was then mixed for 30 minutes and filtered using the above noted filters in the order listed.

Table III shows an antifreeze/coolant and metals analysis of a spent antifreeze/coolant before treatment by the process of this invention. The analyses were conducted by ICP (Inductively Coupled Plasma) analysis. Tables IV and V show the result of ICP analysis of several metals and compounds in their soluble and insoluble forms both after a treatment step according to the instant invention. Tables IV and V demonstrate the effectiveness of the instant process in removing heavy metals, particularly lead and molybdenum, from spent antifreeze/coolant compositions. Referring to Table V, it is shown that in one embodiment of the instant process that after treatment the concentrations of the soluble forms of potassium, molybdenum, boron, iron, phosphorus and silicon are reduced. The insoluble forms of aluminum, calcium, iron, magnesium, sodium, silicon, phosphorus, lead and zinc were reduced. Further, reference to Table IV demonstrates the ability of the instant process to remove TTZ and benzoate as well as reduce the total suspended solids in the treated antifreeze/coolant.

It is particularly important to note that after treatment according to the invention that no detectable lead was present in the antifreeze/coolant down to the detection limits of ICP analysis (less than about 2 ppm). Further, since the antifreeze/coolant was passed through a 5 micron filter and the cation exchange resin (having an effective filter size of 2.0 microns) the final treated antifreeze/coolant meets current regulations of the Environmental Protection Agency for being a non-hazardous material on the basis of lead content. (40 C.F.R. 261.24). Further, it has been observed that the form of the heavy metals in the instant precipitate is such that the heavy metals are not leachable by water.

TABLE III

A. ANTIFREEZE/COOLANT COMPOSITION BEFORE CHEMICAL TREATMENT[1]

| | |
|---|---|
| pH | 9.42 |
| EG Wt % | 32.2 |
| DEG Wt % | 1.2 |
| PG Wt % | 0.6 |
| Cl | 25 |
| SO$_4$ | 91 |
| TTZ | 262 |
| NO$_2$ | ND |
| NO$_3$ | 472 |
| Benzoate | 652 |
| TSS | 650 |

[1]Values are in micrograms per milliliter; ND means not detected at 2 ppm or higher.

B. SOLUBLE SPECIES BEFORE TREATMENT

| ELEMENT | AVERAGE[1] |
|---|---|
| Al | ND |
| B | 179.8 |
| Ca | ND |
| Cu | ND |
| Fe | 11.5 |
| K | 334.9 |
| Mg | ND |
| Mo | 9.7 |
| Na | 1509.0 |
| P | 464.0 |
| Pb | ND |
| Si | 70.7 |
| Sn | ND |
| Zn | ND |

C. INSOLUBLE SPECIES BEFORE TREATMENT

| ELEMENT | AVERAGE[1] |
|---|---|
| Al | 13.6 |
| B | 9.9 |
| Ca | 10.2 |
| Cu | ND |
| Fe | 80.7 |
| K | ND |
| Mg | 3.5 |
| Mo | ND |
| Na | 47.5 |
| P | 24.9 |
| Pb | 26.6 |
| Si | 10.7 |
| Sn | ND |
| Zn | 7.4 |

[1]Values are in ppm; ND means not detected at 2 ppm or higher.

TABLE IV

| ELEMENT[1] MEASURED | AFTER 50 u FILTER | AFTER 40 u FILTER | AFTER CARBON FILTER | AFTER 5 u FILTER | AFTER CATION EXCHANGE RESIN |
|---|---|---|---|---|---|
| Wt % EG(GC) | 28.3 | 28.5 | 28.3 | 28.5 | 28.5 |
| Wt % EG(RI) | 29.9 | 30.0 | 29.8 | 30.0 | 30.0 |
| pH | 6.7 | 6.8 | 6.7 | 6.8 | 7.9 |
| Wt % DEG | 1.05 | 1.02 | 0.98 | 0.99 | 0.96 |
| Wt % PG | 0.51 | 0.51 | 0.51 | 0.48 | 0.51 |
| F | 76 | 74 | 75 | 76 | 77 |
| Cl | 23 | 23 | 23 | 23 | 25 |
| SO$_4$ | 96 | 97 | 98 | 97 | 107 |
| TTZ | 206 | 235 | 90 | 101 | 61 |
| NO$_3$ | 3141 | 3017 | 2759 | 3103 | 3105 |
| BENZOATE | 325 | 318 | 250 | 232 | 247 |
| TSS/PPM | 456 | 112 | 68 | 36 | 24 |

TABLE V

| | AFTER 50 MICRON BAG | | AFTER 40 MICRON FILTER | |
|---|---|---|---|---|
| | SOL | INS | SOL | INS |
| Al | ND | 131.7 | ND | 11.7 |
| B | 155.8 | 16.8 | 161.8 | 9.7 |
| Ca | ND | 6.8 | ND | 4.0 |
| Cu | ND | ND | ND | ND |
| Fe | ND | 32.2 | ND | ND |
| K | 499.5 | 23.3 | 513.1 | ND |
| Mg | ND | 2.0 | ND | ND |
| Mo | 7.7 | ND | 8.1 | ND |

TABLE V-continued

| | | | | |
|---|---|---|---|---|
| Na | 1414 | 73.2 | 1434 | 21.6 |
| P | 190.9 | 161.2 | 194.7 | 7.8 |
| Pb | ND | ND | ND | ND |
| Si | 34.7 | 11.8 | 35.4 | 12.2 |
| Sn | ND | ND | ND | ND |
| Zn | ND | 3.8 | ND | ND |

| | AFTER CARBON | | AFTER 5 MICRON FILTER | | AFTER CATION EXCHANGE RESIN | |
|---|---|---|---|---|---|---|
| ELEMENT | SOL | INS | SOL | INS | SOL | INS |
| Al | ND | 21.1 | ND | 3.2 | ND | 4.0 |
| B | 162.3 | 10.7 | 156.3 | 8.6 | 147.2 | 11.6 |
| Ca | 2.6 | 4.0 | 2.1 | 2.3 | 2.2 | 3.1 |
| Cu | ND | ND | ND | ND | ND | ND |
| Fe | ND | 3.1 | ND | ND | ND | ND |
| K | 526.7 | ND | 509.6 | ND | 252.3 | ND |
| Mg | ND | ND | ND | ND | ND | ND |
| Mo | 8.7 | ND | 8.3 | ND | ND | ND |
| Na | 1495 | 27.1 | 1440 | 19.2 | 1962 | 29.3 |
| P | 205.1 | 18.6 | 199.0 | ND | 202.0 | ND |
| Pb | ND | ND | ND | ND | ND | ND |
| Si | 34.8 | 3.9 | 33.9 | 3.0 | 33.7 | 6.5 |
| Sn | ND | ND | ND | ND | ND | ND |
| Zn | ND | ND | ND | ND | ND | ND |

EXAMPLE 3

A spent antifreeze/coolant was obtained from a commercial establishment in the business of changing over spent antifreeze/coolant from automobiles and trucks. A portion of spent antifreeze was treated according to one of the following chemical treatments to demonstrate the effect of changes in the pH-adjusting agent, precipitating agent, coagulant and flocculant on the treatment process. The coagulant in each treatment was Calgon 2466 and the flocculant was Calgon 7736. The treatment process was carried out and the analysis conducted as set forth, except as noted below in Example 2 for following ten (10) different chemical treatments and except the antifreeze/coolant sample size which was treated was 500 milliliters.

| TREATMENT NO. | CHEMICAL TREATMENT |
|---|---|
| 1 | The pH of the sample was adjusted to about 7.0 with organic acid (acetic acid - $CH_3COOH$, 99.7% solution); by treatment with 0.75 ml of organic acid followed by addition of 1.3 grams of $Al(NO_3)_3 \cdot 9H_2O$, followed by addition of 30 milliliters (ml) coagulant (0.25% volume) solution, and then followed by addition of 10 ml. of 0.25% flocculant solution. |
| 2 | The pH of the sample was adjusted to about 7.0 with 1.9 grams of $Ca(NO_3)_2 \cdot 2H_2O$ (without addition of any pH adjusting agent, coagulant and flocculant). |
| 3 | The pH of the sample was adjusted to about 7.0 with 0.75 ml of inorganic acid (70 wt % nitric acid, followed by treatment with 1.3 grams of $Al(NO_3)_3 \cdot 9H_2O$ as the precipitating agent and then followed by addition of 30 ml of a 0.25% solution of the coagulant. |
| 4 | The pH of the sample was adjusted to about 7.0 with 0.75 ml of nitric acid solution (70 wt % $HNO_3$), followed by addition of 1.3 grams $Al(NO_3)_3 \cdot 9H_2O$ as a precipitating agent, followed by addition of a 10 ml of 0.25 wt % solution of the flocculant. |
| 5 | The pH of the sample was adjusted to about 7.0 with 0.75 ml, nitric acid aqueous solution (70 wt % $HNO_3$); followed by addition of 1.3 grams of $Al(NO_3)_3 \cdot 9H_2O$, followed by addition of 10 ml of a 0.25 wt % aqueous solution of the flocculant, and then followed by addition of 30 ml of a 0.25 wt % solution (aqueous) of the coagulant. |
| 6 | The pH of the sample was adjusted to a pH of about 7.0 by addition of 0.75 ml of aqueous nitric acid (70 wt % $HNO_3$), followed by treatment with 1.3 grams $Al(NO_3)_3 \cdot 9H_2O$, followed by addition of 10 ml of a 0.25 wt % solution coagulant, and then 30 ml of the 0.25 wt % aqueous flocculant solution. |
| 7 | The pH of the sample was adjusted to about pH 7.0 with 0.75 ml aqueous nitric acid (70 wt % $HNO_3$); and then mixed with 1.3 grams $Al(NO_3)_3 \cdot 9H_2O$ followed by addition of 30 ml of a 0.25 wt % aqueous solution of coagulant, and then followed by addition of 10 ml of a 0.25 wt % aqueous solution of flocculant. |
| 8 | The pH of the sample was adjusted to about pH 7.0 with 0.75 ml of nitric acid (70% $HNO_3$); followed by treatment with 1.3 grams $Al(NO_3)_3 \cdot 9H_2O$ followed by addition of 15 ml of a 0.5 wt % solution of coagulant and then followed by addition of 5 ml of a 0.5 wt % solution of the flocculant. |
| 9 | The pH of the sample was adjusted to about pH 7.0 by addition of 0.7 ml of an aqueous formic acid solution (88% Formic acid - HCOOH) followed by addition of 1.3 grams of $Al(NO_3)_3 \cdot 9H_2O$, followed by addition of 30 ml of a 25 wt aqueous solution of coagulant, and then followed by addition of 10 ml of a 0.25 wt % aqueous solution of flocculant. |
| 10 | The sample was treated with 30 ml of a 0.25 wt % aqueous solution of the coagulant and with 10 ml of a 0.25 wt % solution of the flocculant (comparative sample without pH-adjusting agent and without precipitating agent). |

Each of the above samples were then filtered through a 25 micron filter and the final treated antifreeze/coolant analyzed. The results of the analyses are set forth in Table VI. Table VI demonstrates that surprising results obtained by use of the adjustment of the pH to between about 4.0 and about 7.5, the use of a precipitating agent and the use of several concentrations of coagulant and flocculant.

TABLE VI

| | TREATMENT NO. | | | | | |
|---|---|---|---|---|---|---|
| | CONTROL[1] | 1 | 2 | 3 | 4 | 5 |
| pH | 9.1 | 5.87 | 7.5 | 5.54 | 5.18 | 5.39 |
| Al, ppm | 15.9 | ND | ND | ND | ND | ND |
| B, ppm | 146.2 | 125 | 147 | 127 | 125 | 125 |
| Ca, ppm | 3.2 | 2.4 | 33.2 | 3.0 | 3.4 | 2.8 |
| Fe, ppm | 24.7 | ND | ND | ND | ND | ND |
| K, ppm | 640.0 | 506 | 604 | 483 | 522 | 490 |
| Mg, ppm | ND[2] | ND | ND | ND | ND | ND |
| Mo, ppm | 16.7 | 12.3 | 12.8 | 11.9 | 12.4 | 12.1 |
| Na, ppm | 1471 | 1319 | 1437 | 1366 | 1367 | 1331 |
| P, ppm | 444 | 142 | 61.9 | 139 | 137 | 140 |
| Pb, ppm | 19.7 | ND | ND | ND | ND | ND |
| Si, ppm | 109.3 | 44.7 | 55.2 | 44.5 | 45.9 | 39.8 |
| Zn, ppm | 7.2 | ND | ND | ND | ND | ND |

| | TREATMENT NO. | | | | |
|---|---|---|---|---|---|
| | 6 | 7 | 8 | 9 | 10 |
| pH | 5.41 | 5.55 | 5.25 | 5.13 | 9.1 |
| Al, ppm | ND | ND | ND | ND | 3 |
| B, ppm | 121 | 127.4 | 130.6 | 129.4 | 128 |
| Ca, ppm | ND | 2.8 | 3.5 | ND | ND |
| Fe, ppm | ND | ND | ND | ND | 3.0 |
| K, ppm | 487 | 490.0 | 506.4 | 517.0 | 507.0 |
| Mg, ppm | ND | ND | ND | ND | ND |
| Mo, ppm | ND | 11.8 | 12.2 | ND | 13.3 |
| Na, ppm | 1350 | 1295 | 1365 | 1426 | 1210 |

TABLE VI-continued

| P, ppm | 136 | 141 | 147 | 139 | 331 |
|---|---|---|---|---|---|
| Pb, ppm | ND | ND | ND | ND | 2.8 |
| Si, ppm | ND | 40.7 | 40.6 | ND | 42.0 |
| Zn, ppm | ND | ND | ND | ND | ND |

[1]Antifreeze/Coolant prior to treatment as obtained from the cooling systems of automobiles/trucks.
[2]"ND" means not detected at 2 ppm or higher.

The results in Table VI demonstrate the adjustment of the pH and use of the precipitating agent (e.g. Treatment Nos. 6 and 9) followed by addition of the coagulant and flocculant was more effective than use of only the coagulant and flocculant (e.g., Treatment No. 10), or by use of only $Ca(NO_3)_2.2H_2O$ as the precipitating agent (Treatment No. 2). When a process according to this invention is employed (as in Treatment Nos. 6 and 9) it is observed that the treated solutions from Treatment Nos. 6 and 9 have reduced concentrations of iron, molybdenum, silicon and zinc below detection limits (2 ppm). Further, while both Treatments 6 and 9 removed detectable solubilized lead, Treatment No. 10 (employing only coagulant and flocculant addition) gave a treated product containing 2.8 ppm Pb, 3.0 ppm Fe, 3.0 ppm Al and 13.3 ppm Mo.

EXAMPLE 4

The process employed in example 3 (Treatment No. 7) was repeated using a propylene glycol-based antifreeze/coolant having the composition shown in Table VII. The propylene glycol-based antifreeze/coolant had been employed as the antifreeze/coolant in an automotive cooling system to provide the "original used antifreeze/coolant" employed in the instant example. The treatments with the pH-adjusting agent ($HNO_3$), precipitating agent ($Al(NO_3)_3.9H_2O$), coagulant (Calgon 2466) and flocculant (Calgon 7736) were conducted as described in Example 3 to provide a treated propylene glycol-based antifreeze/coolant as shown in Table VII, below. As shown in Table VII, the instant process was effective in removing an amount of potassium, phosphorus and Total Suspended Solids and from the original used antifreeze/coolant. Since the original used antifreeze/coolant did not contain several metals at detection levels above about 2 ppm, the removal of these metals by the process of this invention could not be quantitatively evaluated.

TABLE VII

| | PROPERTIES OF ANTIFREEZE/COOLANT | |
|---|---|---|
| TEST | ORIGINAL USED ANTIFREEZE/COOLANT | AFTER TREATMENT |
| pH | 8.2 | 6.1 |
| PG, % | 52.5 | 49.8 |
| TTZ | 28 | 26.0 |
| Benzoate | ND | ND |
| NO3 | 803 | 3700 |
| SO4 | 171 | 152 |
| F | 80 | 66 |
| Cl | 50 | 50 |
| TSS | 238 | 14 |
| Al, ppm | ND | ND |
| B, ppm | 367.1 | 307.4 |
| Ca, ppm | ND | ND |
| Cu, ppm | ND | ND |
| Fe, ppm | ND | ND |
| K, ppm | 94 | 59.5 |
| Mg, ppm | ND | ND |
| Mo, ppm | ND | ND |
| Na, ppm | 2083 | 1759 |
| P, ppm | 749.8 | 285.4 |
| Pb, ppm | ND | ND |
| Si, ppm | 57 | 48.8 |
| Sn, ppm | ND | ND |
| Zn, ppm | ND | ND |

EXAMPLE 5

A reinhibited, used antifreeze/coolant ("AC") according to the instant invention is prepared from a recycled antifreeze/coolant obtained from a commercial recycle process. The chemical fingerprint for the recycled antifreeze/coolant is set forth as well as the final concentrations of the chemical components in the final reinhibited antifreeze/coolant. Further, the concentrations of chemical components (based upon the addition of 4 oz. of each additive per U.S. gallon (128 oz.) of recycled antifreeze/coolant in the two additives employed to achieve the final antifreeze/coolant are set forth as two additive packages ("A" and "A") employed by adding additive package "A" to the recycled antifreeze/coolant followed by addition of additive package B. Phosphorus is assumed to be phosphate; boron is assumed to be borate; and silicon is assumed to be silicate and silicone. The chemical components in each package are as follows:

| PACKAGE A | PACKAGE B |
|---|---|
| Ethylene Glycol (EG) | Ethylene Glycol (EG) |
| Water | Water |
| NaOH | TTZ |
| MBT | Borax, 20% in EG |
| Sodium Molybdate | Phosphoric Acid |
| Silicone | Antifoam |
| Na Silicate | Dye |
| Dye | |

Correlation according to the current invention results in the following:

| | RECYCLED AC (ppm) | FINAL AC (ppm) | ADDITIVES (ppm) |
|---|---|---|---|
| PHOSPHORUS | 0 | 782.0 | 26588 |
| BORON | 118 | 295.0 | 6264 |
| NITRATE | 843 | 729.0 | 0 |
| SILICON | 37 | 227.0 | 6534 |
| TTZ | 178 | 745.0 | 19634 |
| ANTIFOAM | | 33.5 | 1139 |
| DYE | | 15.0 | 510 |
| DYE | | 10.0 | 340 |
| SODIUM HYDROXIDE | — | — | —[1] |

[1]Sodium hydroxide is added to adjust pH to between about 9 to about 10.5.

EXAMPLE 6

A reinhibited, used antifreeze/coolant ("AC") according to the instant invention is prepared from a recycled antifreeze/coolant obtained from a commercial recycle process. The chemical fingerprint for the recycled antifreeze/coolant is set forth as well as the final concentrations of the chemical components in the final reinhibited antifreeze/coolant. Further, the concentrations of chemical components (based upon the addition of 4 oz. of each additive per gallon of recycled antifreeze/coolant) in the two additives employed to achieve the final antifreeze/coolant is set forth as two additive packages ("A" and "A") employed by adding additive package "A" to the recycled antifreeze/coolant followed by addition of additive package B. Phosphorus is assumed to be phosphate; boron assumed to be borate; and silicon is assumed to be silicate and silicone. The chemical components in each package are as follows:

| PACKAGE A | PACKAGE B |
| --- | --- |
| Ethylene Glycol (EG) | Ethylene Glycol (EG) |
| Water | Water |
| NaOH | TTZ |
| MBT | Borax, 20% in EG |
| Sodium Molybdate | Phosphoric Acid |
| Silicone | Antifoam |
| Na Silicate | Dye |
| Dye | |

Correlation according to the current invention results in the following:

| | RECYCLED AC (ppm) | FINAL AC (ppm) | ADDITIVES (ppm) |
| --- | --- | --- | --- |
| PHOSPHORUS | 0 | 828.0 | 28152 |
| BORON | 118 | 186.0 | 2548 |
| NITRATE | 846 | 905.0 | 3698 |
| SILICON | 37 | 240.0 | 6976 |
| TTZ | 178 | 542.0 | 12732 |
| ANTIFOAM | | 33.5 | 1139 |
| DYE | | 15.0 | 510 |
| DYE | | 10.0 | 340 |
| SODIUM HYDROXIDE | — | — | —[1] |

[1]Sodium hydroxide is added to adjust pH to between about 9 to about 10.5.

EXAMPLE 7

A reinhibited, used antifreeze/coolant ("AC") according to the instant invention is prepared from a recycled antifreeze/coolant obtained from the recycle process of U.S. Ser. No. 07/564,262, filed Aug. 8, 1990. The chemical fingerprint for the recycled antifreeze/coolant is set forth as well as the final concentrations of the chemical components in the final reinhibited antifreeze/coolant. Further, the concentrations of chemical components (based upon the addition of 4 oz. of each additive per U.S. gallon (128 oz.) of recycled antifreeze/coolant) in the two additives employed to achieve the final antifreeze/coolant is set forth as two additive packages ("A" and "A") employed by adding additive package "A" to the recycled antifreeze/coolant followed by addition of additive package B. Phosphorus is assumed to be phosphate; boron is assumed to be borate; and silicon is assumed to be silicate and silicone. The chemical components in each package are as follows:

| PACKAGE A | PACKAGE B |
| --- | --- |
| Ethylene Glycol (EG) | Ethylene Glycol (EG) |
| Water | Water |
| NaOH | TTZ |
| MBT | Borax, 20% in EG |
| Sodium Molybdate | Phosphoric Acid |
| Silicone | Antifoam |
| Na Silicate | Dye |
| Dye | |

Correlation according to the current invention results in the following:

| | RECYCLED AC (ppm) | FINAL AC (ppm) | ADDITIVES (ppm) |
| --- | --- | --- | --- |
| PHOSPHORUS | 261 | 782.0 | 18236 |
| BORON | 186 | 295.0 | 4078 |
| NITRATE | 3500 | 729.0 | 0 |
| SILICON | 61 | 227.0 | 5766 |
| TTZ | 114 | 248.0 | 4784 |
| ANTIFOAM | | 33.5 | 1139 |
| DYE | | 15.0 | 510 |
| DYE | | 10.0 | 340 |
| SODIUM HYDROXIDE | — | — | —[1] |

[1]Sodium hydroxide is added to adjust pH to between about 9 to about 10.5.

EXAMPLE 8

A reinhibited, used antifreeze/coolant ("AC") according to the instant invention is prepared from a recycled antifreeze/coolant obtained from the recycle process of U.S. Ser. No. 07/564,262, filed Aug. 8, 1990. The chemical fingerprint for the recycled antifreeze/coolant is set forth as well as the final concentrations of the chemical components in the final reinhibited antifreeze/coolant. Further, the concentrations of chemical components (based upon addition of 4 oz. of each additive per U.S. gallon (128 oz.) of recycled antifreeze/coolant) in the two additives employed to achieve the final antifreeze/coolant are set forth as two additive packages ("A" and "A") employed by adding additive package "A" to the recycled antifreeze/coolant followed by addition of additive package B. Phosphorus is assumed to be phosphate; boron is assumed to be borate; and silicon is assumed to be silicate and silicone. The chemical components in each package are as follows:

| PACKAGE A | PACKAGE B |
| --- | --- |
| Ethylene Glycol (EG) | Ethylene Glycol (EG) |
| Water | Water |
| NaOH | TTZ |
| MBT | Borax, 20% in EG |
| Sodium Molybdate | Phosphoric Acid |
| Silicone | Antifoam |
| Na Silicate | Dye |
| Dye | |

Correlation according to the current invention results in the following:

| | RECYCLED AC (ppm) | FINAL AC (ppm) | ADDITIVES (ppm) |
| --- | --- | --- | --- |
| PHOSPHORUS | 261 | 782.0 | 18236 |
| BORON | 186 | 295.0 | 4078 |
| NITRATE | 3500 | 729.0 | 0 |
| SILICON | 61 | 279.0 | 7534 |
| TTZ | 114 | 745.0 | 21682 |
| ANTIFOAM | | 33.5 | 1139 |
| DYE | | 15.0 | 510 |
| DYE | | 10.0 | 340 |
| SODIUM HYDROXIDE | — | — | —[1] |

[1]Sodium hydroxide is added to adjust pH to between about 9 to about 10.5.

EXAMPLE 9

A reinhibited, used antifreeze/coolant ("AC") according to the instant invention was prepared from a recycled antifreeze/coolant obtained from the recycle process commercially available from BG Products, Inc. The chemical fingerprint for the recycled antifreeze/coolant is set forth as well as the final concentrations of the chemical components in the final reinhibited antifreeze/coolant. Further, the concentrations of chemical components (based upon addition of 4 oz. of each additive per U.S. gallon (128 oz.) of recycled antifreeze/coolant) in the two additives employed to achieve the final antifreeze/coolant are set forth as two additive packages ("A" and "A") employed by adding additive package "A" to the recycled antifreeze/coolant followed by addition of additive package B. Phosphorus is assumed to be phosphate; boron is assumed to be borate; and silicon is assumed to be silicate and silicone. The chemical components in each package are as follows:

| PACKAGE A | PACKAGE B |
| --- | --- |
| Ethylene Glycol (EG) | Ethylene Glycol (EG) |
| Water | Water |
| NaOH | TTZ |
| MBT | Borax, 20% in EG |
| Sodium Molybdate | Phosphoric Acid |
| Silicone | Antifoam |
| Na Silicate | Dye |
| Dye | |

Correlation according to the current invention resultts in the following:

| | RECYCLED AC (ppm) | FINAL AC (ppm) | ADDITIVES (ppm) |
| --- | --- | --- | --- |
| PHOSPHORUS | 0 | 782.0 | 26588 |
| BORON | 0 | 295.0 | 10030 |
| NITRATE | 0 | 729.0 | 24786 |
| SILICON | 12 | 227.0 | 7718 |
| TTZ | 0 | 745.0 | 25330 |
| ANTIFOAM | | 33.5 | 1139 |
| DYE | | 15.0 | 510 |
| DYE | | 10.0 | 340 |
| SODIUM HYDROXIDE | — | — | —[1] |

[1] Sodium hydroxide is added to adjust pH to between about 9 to about 10.5.

EXAMPLE 10

A reinhibited, used antifreeze/coolant ("AC") according to the instant invention is prepared from a recycled antifreeze/coolant obtained from the recycle process of U.S. Pat. No. 4,946,595. The chemical fingerprint for the recycled antifreeze/coolant is set forth as well as the final concentrations of the chemical components in the final reinhibited antifreeze/coolant. Further, the concentrations of chemical components (based upon the addition of 4 oz. of each additive per U.S. gallon (128 oz.) of recycled antifreeze/coolant) in the two additives employed to achieve the final antifreeze/coolant are set forth as two additive packages ("A" and "A") employed by adding additive package "A" to the recycled antifreeze/coolant followed by addition of additive package B. Phosphorus is assumed to be phosphate; boron is assumed to be borate; and silicon is assumed to be silicate and silicone. The chemical components in each package are as follows:

| PACKAGE A | PACKAGE B |
| --- | --- |
| Ethylene Glycol (EG) | Ethylene Glycol (EG) |
| Water | Water |
| NaOH | TTZ |
| MBT | Borax, 20% in EG |
| Sodium Molybdate | Phosphoric Acid |
| Silicone | Antifoam |
| Na Silicate | Dye |
| Dye | |

Correlation according to the current invention results in the following:

| | RECYCLED AC (ppm) | FINAL AC (ppm) | ADDITIVES (ppm) |
| --- | --- | --- | --- |
| PHOSPHORUS | 669 | 828.0 | 5784 |
| BORON | 267 | 186.0 | 0 |
| NITRATE | 780 | 905.0 | 5810 |
| SILICON | 131 | 542.0 | 5564 |
| TTZ | 402 | 542.0 | 5564 |
| ANTIFOAM | | 33.5 | 1139 |
| ALIZARINE | | 15.0 | 510 |
| URANINE | | 10.0 | 340 |
| SODIUM HYDROXIDE | — | — | —[1] |

[1] Sodium hydroxide is added to adjust pH to between about 9 to about 10.5.

We claim:

1. A process for the reinhibition of a recycled antifreeze/coolant of an internal combustion engine, said antifreeze/coolant being the product of a recycle process wherein said reinhibition process comprises correlating at a preselected effective corrosion inhibiting amount the chemical composition of a reinhibitor package to the chemical composition of said recycled antifreeze/coolant by adding an amount of at least one corrosion inhibitor effective in inhibiting the corrosion of at least one metal in said cooling system whereby a reinhibited, recycled antifreeze/coolant is formed by providing said preselected corrosion inhibition.

2. A process according to claim 1 wherein said recycled antifreeze/coolant contains at least one corrosion inhibitor to be added in said inhibitor package to a residual concentration of said corrosion inhibitor in said recycled antifreeze/coolant below the effective corrosion inhibiting amount.

3. A process according to claim 1 wherein said recycled antifreeze/coolant, reinhibitor package and reinhibited, recycled coolant are correlated to provide a preselected corrosion inhibition for said reinhibited recycled antifreeze/coolant by correlating the concentrations of at least one component selected from the group consisting of borate, phosphate, silicate, silicone, azole and molybdate.

4. A process according to claim 1 wherein the effective concentrations of corrosion inhibitors in said reinhibitor package is correlated to the concentrations of corrosion inhibitors in the recycled antifreeze/coolant by adjusting the concentration of said corrosion inhibitors in relation to the concentration in said recycled antifreeze/coolant wherein said reinhibitor package is provided as a first additive and a second additive, said first additive containing an effective amount of a base-stabilized silicate at a pH above about 12 and a second additive having a pH less than 12 containing an effective amount of at least one corrosion inhibitor and containing at least one buffering agent wherein said first additive is added to said recycled antifreeze/coolant prior to said addition of said second additive.

5. A process according to claim 4 wherein said base-stabilized silicate is silicone stabilized in the reinhibited, recycled antifreeze/coolant.

6. A process according to claim 1 wherein the pH of the reinhibited, recycled antifreeze/coolant is between about 8.5 and about 11.5.

7. A process according to claim 6 wherein the pH of the reinhibited, recycled antifreeze/coolant is between about 9.0 and 10.5.

8. A process according to claim 6 wherein the reinhibited antifreeze/coolant has a preselected reserve alkalinity.

9. A process according to claim 1 wherein said aqueous composition is a heavy metal-containing polyhydric alcohol-containing antifreeze/coolant taken from the cooling system of an internal combustion engine of an automobile.

10. A process according to claim 9 wherein said cooling system is an automotive cooling system and said heavy metal is at least one heavy metal selected from the group consisting of lead, molybdenum, iron, zinc, and copper.

11. A process according to claim 9 wherein said polyhydric alcohol is ethylene glycol.

12. A process according to claim 11 wherein said ethylene glycol is present in an amount of between 30 and 70 volume percent.

13. A process according to claim 9 wherein said polyhydric alcohol is selected from the group consisting of ethylene glycol, diethylene glycol, propylene glycol, dipropylene glycol, glycerol, butene glycol, the monoacetate of propylene glycol, the monoethylether of glycerol, the dimethyl ether of glycerol, alkoxy alkanols and mixture thereof.

14. A process according to claim 13 wherein said polyhydric alcohol is selected from the group consisting of ethylene glycol, diethylene glycol, propylene glycol and mixtures thereof.

15. A process according to claim 1 wherein said recycle process comprises a treatment of an aqueous composition containing between about 5 weight percent and about 95 weight percent of a polyhydric alcohol wherein said aqueous composition is an antifreeze/coolant taken from the cooling system of an internal combustion engine having a pH and containing at least one heavy metal wherein said process comprises:

(i) removing said antifreeze/coolant from said cooling system and then adjusting the pH of said aqueous composition to between about 4.0 and about 7.5 by addition of an effective amount of a pH adjusting agent to form a pH-adjusted composition and adding thereto an effective amount of a precipitating agent for said heavy metal to form a precipitate.

16. A process according to claim 15 wherein said recycle process comprises the following additional step:

(ii) skimming a portion of said precipitate from said pH adjusted composition of step (i).

17. A process according to claim 15 wherein the pH in step (i) is adjusted to between about 4.5 and about 7.0.

18. A process according to claim 15 wherein said precipitating agent is selected from the group consisting of chlorides, sulfates, phosphates, aluminum nitrates and mixtures thereof.

19. A process according to claim 15 wherein said process is carried out at a temperature between about 18° C. and about 45° C.

20. A process according to claim 15 wherein the pH-adjusting agent is at least one pH-adjusting agent selected from the group consisting of organic acids, inorganic acid acidic organic salts, acidic inorganic salts and mixtures thereof.

21. A process according to claim 20 wherein the pH-adjusting agent is selected from the group consisting of nitric acid, phosphoric acid, sulfuric acid, hydrochloric acid, carboxylic acids and mixtures thereof.

22. A process according to claim 21 wherein said pH-adjusting agent is nitric acid.

23. A process according to claim 15 wherein said recycle process comprises the following additional steps:

(ii) adding to the pH-adjusted composition an effective amount of coagulating agent and an effective amount of a flocculating agent to form a precipitate containing at least one heavy metal; and (iii) passing the pH-adjusted composition through a first filtration means to remove heavy metal-containing precipitate from said pH-adjusted composition.

24. A process according to claim 23 wherein said recycle process comprises the following additional steps of:

(iv) passing said pH-adjusted composition of step (iii) through a second filtration means having an effective physical separation of greater than about 40 microns;

(v) passing the pH-adjusted composition from step (iv) through an organic separation means effective in removing organic compounds other than said polyhydric alcohol from said pH-adjusted composition;

(vi) passing said pH-adjusted composition through a third filtration means having an effective physical separation of greater than about 0.2 microns; and (vii) passing said pH-adjusted composition of step (vi) through an ion exchange effective in the removal of at least one solubilized heavy metal present in said pH-adjusted composition.

25. A process according to claim 23 wherein the flocculating agent is selected from the group consisting of cationic flocculating agents.

26. A process according to claim 23 wherein the coagulating agent is selected from the group consisting of cationic coagulating agents.

27. A process according to claim 23 wherein said coagulating agent is between about 75 ppm and about 300 ppm and said flocculating agent is between about 25 ppm and about 300 ppm.

28. A process according to claim 23 wherein said aqueous composition is obtained from a cooling system of an internal combustion engine contains 5 volume percent to 95 volume percent ethylene glycol, contains up to about 150 ppm lead, said pH-adjusting agent is nitric acid, said precipitating agent is $Al(NO_3)_3 \cdot 9H_2O$ said coagulating agent is present in an amount between about 75 ppm and about 300 ppm, said flocculating agent is present in an amount between about 25 ppm and about 300 ppm.

29. A process according to claim 23 wherein said first filtration means has an effective separation for species greater than about 100 microns.

30. A process according to claim 23 wherein:

(a) said first filtration means has an effective separation for species greater than 100 microns;

(b) providing a second filtration means having effective separation for species greater than 40 microns;

(c) providing organic separation means comprising an activated carbon filter;

(d) providing a third filtration means having effective separation for species greater than 5 microns; and (e) providing ion-exchange means comprising a cation exchange means effective in removal of at least one heavy metal.

31. A process according to claim 1 wherein the recycle process comprises treatment of an aqueous antifreeze/coolant composition obtained from the cooling system of internal combustion engines containing between about 5 weight percent and about 95 weight percent of a polyhydric alcohol selected from the group consisting of ethylene glycol, diethylene glycol and propylene glycol and mixtures thereof and containing at least one solubilized heavy metal species selected from the group consisting of lead, molybdenum, iron, zinc, and copper, wherein said process comprises the following steps:

(i) adjusting the pH of said antifreeze/coolant composition to between about 4.0 and about 7.5 by addition of an effective amount of a pH adjusting agent to form a pH-adjusted composition and adding an effective amount of a precipitating agent effective in forming a precipitate of said heavy metal;

(ii) adding to the said pH-adjusted composition an effective amount of at least one of a coagulating agent and a flocculating agent to form a heavy metal containing precipitate;

(iii) passing said pH-adjusted composition of step (ii) and said heavy metal containing precipitate through a first filtration means effective in removal of said heavy metal-containing precipitate having a size greater than about 100 microns;

(iv) passing said pH-adjusted composition of step (iii) through a second filtration means having an effective physical separation of greater than about 40.0 microns;

(v) passing the pH-adjusted composition from step (iv) through an organic separation means effective in removing organic compounds from said polyhydric alcohol of said pH-adjusted composition;

(vi) passing said pH-adjusted composition through a third filtration means having effective physical separation of greater than about 5 microns; and (vii) passing said pH-adjusted composition of step (vi) through a cation exchange means effective in the removal of at least one solubilized heavy metal species present in said pH-adjusted composition from step (vi).

32. A process according to claim 31 wherein said process comprises the additional step of:

(viii) passing said pH-adjusted composition of step (vii) through water removal means whereby between about 10 weight percent and about 100 weight percent of said water is removed from said pH-adjusted composition.

33. A process according to claim 31 wherein said heavy metal is lead.

34. A process according to claim 31 wherein said polyhydric alcohol comprises a mixture of ethylene glycol and diethylene glycol.

35. A process according to claim 34 wherein said ethylene glycol is present in an amount of between 30 and 70 volume percent.

36. A process according to claim 31 wherein said cooling system is an automotive cooling system and said heavy metal is at least one heavy metal selected from the group consisting of lead, molybdenum, iron, and copper.

37. A process according to claim 31 wherein said polyhydric alcohol is propylene glycol.

38. A process according to claim 31 wherein the pH in step (i) is between about 4.5 and about 7.5.

39. A process according to claim 31 wherein the pH-adjusting agent is at least one pH-adjusting agent selected from the group consisting of organic acids, inorganic acids, acidic organic salts, acidic inorganic salts and mixtures thereof.

40. A process according to claim 39 wherein the pH-adjusting agent is selected from the group consisting of nitric acid, phosphoric acid, sulfuric acid, hydrochloric acid, carboxylic acids and mixtures thereof.

41. A process according to claim 40 wherein said pH-adjusting agent is nitric acid.

42. A process according to claim 31 wherein said precipitating agent is selected from the group consisting of chlorides, sulfates, phosphates, aluminum nitrates, and mixtures thereof.

43. A process according to claim 31 wherein the flocculating agent is selected from the group consisting of cationic flocculating agents.

44. A process according to claim 31 wherein the coagulating agent is selected from the group consisting of cationic coagulating agents.

45. A process according to claim 31 wherein flocculating agent is an anionic flocculant and the coagulating agent is a cationic coagulating agent.

46. A process according to claim 31 wherein said coagulating agent is between about 75 ppm and about 300 ppm and said flocculating agent is between about 25 ppm and about 100 ppm.

47. A process according to claim 31 wherein said spent antifreeze/coolant composition contains 5 volume percent to 95 volume percent ethylene glycol, contains up to 250 ppm lead, said pH-adjusting agent is nitric acid, said precipitating agent is $Al(NO_3)_3.9H_2O$ said coagulating agent is present in an effective amount between about 75 ppm and about 300 ppm and said flocculating agent is present in an effective amount between about 25 ppm, and about 300 ppm.

48. A process according to claim 31 wherein said precipitate contains lead from said aqueous antifreeze/coolant composition.

* * * * *